United States Patent
Lu et al.

(10) Patent No.: US 7,863,315 B2
(45) Date of Patent: Jan. 4, 2011

(54) 2-INDOLINONE DERIVATIVES AS SELECTIVE HISTONE DEACETYLASE INHIBITORS

(75) Inventors: Xian-Ping Lu, Belle Meade, NJ (US); Zhi-bin Li, Shenzhen (CN); Zhi-Qiang Ning, Shenzhen (CN)

(73) Assignee: Shenzhen Chipscreen Biosciences, Ltd., Shenzhen, Guangdong (JP)

( * ) Notice: Subject to any disclaimer, the term of this patent is extended or adjusted under 35 U.S.C. 154(b) by 163 days.

(21) Appl. No.: 12/353,566

(22) Filed: Jan. 14, 2009

(65) Prior Publication Data

US 2009/0182029 A1    Jul. 16, 2009

Related U.S. Application Data

(60) Provisional application No. 61/006,463, filed on Jan. 15, 2008.

(51) Int. Cl.
*A61K 31/404* (2006.01)
*C07D 209/04* (2006.01)
*C07D 209/10* (2006.01)

(52) U.S. Cl. .................. 514/416; 514/418; 514/419; 548/483; 548/484

(58) Field of Classification Search ............... 514/416, 514/418, 419; 548/483, 484
See application file for complete search history.

(56) References Cited

U.S. PATENT DOCUMENTS 6,541,503 B2 * 4/2003 Davis et al. ............. 514/414
2002/0103192 A1 8/2002 Curtin et al.

FOREIGN PATENT DOCUMENTS

| EP | 0847992 A1 | 6/1998 |
| WO | WO0118171 A2 | 3/2001 |
| WO | WO0170675 A2 | 9/2001 |
| WO | WO0226696 A1 | 4/2002 |

OTHER PUBLICATIONS

STN-12353566-08052010.*
de Ruijter, A. J. M., et al., "Histone Deacetylases (HDACs): Characterization of the Classical HDAC Family", Biochemical Journal, 2003, vol. 370, pp. 737-749.
Marks, P. A. et al., "Histone Deacetylases and Cancer: Causes and Therapies", Nature Reviews Cancer, 2001, vol. 1, pp. 194-202.
Dokmanovic, M. et al., "Prospects: Histone Deacetylase Inhibitors", Journal of Cellular Biochemistry, 2005, vol. 96, pp. 293-304.
Herman, D. et al., "Histone Deacetylase Inhibitors Reverse Gene Silencing in Friedreich's Ataxia", Nature Chemical Biology, 2006, vol. 2, No. 10, pp. 551-559.
Lagger, G. et al., "Essential Function of Histone Deacetylase 1 in Proliferation Control and CDK Inhibitor Repression", The EMBO Journal, 2002, vol. 21, No. 11, pp. 2672-2681.
Bartl, S. et al., "Identification of Mouse Histone Deacetylase 1 as a Growth Factor-Inducible Gene", Molecular and Cellular Biology, 1997, vol. 17, No. 9, pp. 5033-5043.
Wilson, A. J. et al., "Histone Deacetylase 3(HDAC3) and Other Class I HDACs Regulate Colon Cell Maturation and p21 Expression and Are Deregulated in Human Colon Cancer", The Journal of Biological Chemistry, 2006, vol. 281, No. 19, pp. 13548-13558.
Sakuma, T. et al., "Aberrant Expression of Histone Deacetylase 6 in Oral Squamous Cell Carcinoma", International Journal of Oncology, 2006, vol. 29, pp. 117-124.
Avila, A. M. et al., "Trichostatin A Increases SMN Expression and Survival in a Mouse Model of Spinal Muscular Atrophy", The Journal of Clinical Investigation, 2007, vol. 117, No. 3, pp. 659-671.
Gialitakis, M. et al., "Coordinate Changes of Histone Modifications and HDAC Mobilization Regulate the Induction of MHC Class II Genes by Trichostatin A", Nucleic Acids Research, 2006, vol. 34, No. 3, pp. 765-772.

* cited by examiner

*Primary Examiner*—Yong Chu
(74) *Attorney, Agent, or Firm*—Eckert Seamans Cherin & Mellott, LLC

(57) ABSTRACT

Provided herein are isolated compounds of formula I:

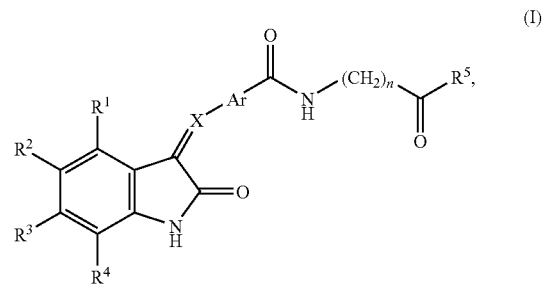

processes for their preparation and isolation, as well as pharmaceutical compositions which comprise these therapeutic agents, and methods of use therefore the treatment and/or control of conditions associated with or mediated by effects of histone deacetylase.

16 Claims, No Drawings

2-INDOLINONE DERIVATIVES AS SELECTIVE HISTONE DEACETYLASE INHIBITORS

Priority is derived from U.S. provisional Ser. No. 61/006,463 filed Jan. 15, 2008.

FIELD OF INVENTION

The present invention relates to certain 2-indolinone derivatives which are capable of inhibiting histone deacetylases. The compounds of this invention are therefore useful in treating diseases associated with abnormal histone deacetylase activities. Pharmaceutical compositions comprising these compounds, methods of treating diseases utilizing pharmaceutical compositions comprising these compounds, and methods of preparing these compounds are also disclosed.

BACKGROUND OF THE INVENTION

Histone deacetylase (HDAC) proteins play a critical role in regulating gene expression in vivo by altering the accessibility of genomic DNA to transcription factors. Specifically, HDAC proteins remove the acetyl group of acetyl-lysine residues on histones, which can result in nucleosomal remodeling (Grunstein, M., 1997, Nature, 389: 349-352). Due to their governing role in gene expression, HDAC proteins are associated with a variety of cellular events, including cell cycle regulation, cell proliferation, differentiation, reprogramming of gene expression, and cancer development (Ruijter, A-J-M., 2003, Biochem. J., 370: 737-749; Grignani, F., 1998, Nature, 391: 815-818; Lin, R-J., 1998, 391: 811-814; Marks, P-A., 2001, Nature Reviews Cancer, 1: 194). The aberrant deacetylation resulting from the misregulation of histone deacetylases (HDACs) has been linked to clinical disorders such as Rubinstein-Taybi syndrome, fragile X syndrome, leukemia, and various cancers (Langley B et al., 2005, Current Drug Targets—CNS & Neurological Disorders, 4: 41-50). In fact, HDAC inhibitors have been demonstrated to reduce tumor growth in various human tissues and in animal studies, including lung, stomach, breast, and prostrate (Dokmanovic, M., 2005, J. Cell Biochem., 96: 293-304).

The aberrant histone deacetylase activity has also been linked to various neurological and neurodegenerative disorders, including stroke, Huntington's disease, Amyotrophic Lateral Sclerosis and Alzheimer's disease. HDAC inhibition may induce the expression of anti-mitotic and anti-apoptotic genes, such as p21 and HSP-70, which facilitate survival. HDAC inhibitors can act on other neural cell types in the central nervous system, such as reactive astrocytes and microglia, to reduce inflammation and secondary damage during neuronal injury or disease. Increase acetylation by HDAC inhibitors induced sprouting of dendrites, an increased number of synapses, and reinstalled learning behavior and access to long-term memories. HDAC inhibitor reverses gene silencing in Friedreich's ataxia These data indicated that HDAC inhibition is a promising therapeutic approach for the treatment of a range of central nervous system disorders (Langley B et al., 2005, Current Drug Targets—CNS & Neurological Disorders, 4: 41-50; Fischer A., et al, 2007, Nature 447(10): 178-183; Herman D., et al., 2006, Nature Chemical Biology 2 (10:551-558).

Mammalian HDACs can be divided into three classes according to sequence homology. Class I consists of the yeast Rpd3-like proteins (HDAC 1, 2, 3, 8 and 11). Class II consists of the yeast HDA1-like proteins (HDAC 4, 5, 6, 7, 9 and 10). Class (III consists of the yeast SIR2-like proteins (SIRT 1, 2, 3, 4, 5, 6 and 7).

The activity of HDAC1 has been linked to cell proliferation, a hallmark of cancer. Particularly, mammalian cells with knock down of HDAC1 expression using siRNA were antiproliferative (Glaser, K-B., 2003, Biochem. Biophys. Res. Comm., 310: 529-536). While the knock out mouse of HDAC1 was embryonic lethal, the resulting stem cells displayed altered cell growth (Lagger, G., 2002, EMBO J., 21: 2672-2681). Mouse cells overexpressing HDAC1 demonstrated a lengthening of $G_2$ and M phases and reduced growth rate (Bartl. S.,1997, Mol. Cell Biol., 17:5033-5043). Therefore, the reported data implicate HDAC1 in cell cycle regulation and cell proliferation.

HDAC2 regulates expression of many fetal cardiac isoforms. HDAC2 deficiency or chemical inhibition of histone deacetylase prevented the re-expression of fetal genes and attenuated cardiac hypertrophy in hearts exposed to hypertrophic stimuli. Resistance to hypertrophy was associated with increased expression of the gene encoding inositol polyphosphate-5-phosphatase f (Inpp5f) resulting in constitutive activation of glycogen synthase kinase 3β (Gsk3β) via inactivation of thymoma viral proto-oncogene (Akt) and 3-phosphoinositide-dependent protein kinase-1 (Pdk1). In contrast, HDAC2 transgenic mice had augmented hypertrophy associated with inactivated Gsk3β. Chemical inhibition of activated Gsk3β allowed HDAC2-deficient adults to become sensitive to hypertrophic stimulation. These results suggest that HDAC2 is an important molecular target of HDAC inhibitors in the heart and that HDAC2 and Gsk3β are components of a regulatory pathway providing an attractive therapeutic target for the treatment of cardiac hypertrophy and heart failure (Trivedi, C-M., 2007, Nat. Med,. 13: 324-331).

HDAC3 are maximally expressed in proliferating crypt cells in normal intestine. Silencing of HDAC3 expression in colon cancer cell lines resulted in growth inhibition, a decrease in cell survival, and increased apoptosis. Similar effects were observed for HDAC2 and, to a lesser extent, for HDAC1. HDAC3 gene silencing also selectively induced expression of alkaline phosphatase, a marker of colon cell maturation. Concurrent with its effect on cell growth, overexpression of HDAC3 inhibited basal and butyrate-induced p21 transcription in a Sp1/Sp3-dependent manner, whereas silencing of HDAC3 stimulated p21 promoter activity and expression. These findings identify HDAC3 as a gene deregulated in human colon cancer and as a novel regulator of colon cell maturation and p21 expression (Wilson, A-J., 2006, J. Biol. Chem., 281: 13548-13558).

HDAC6 is a subtype of the HDAC family that deacetylates alpha-tubulin and increases cell motility. Using quantitative real-time reverse transcription polymerase chain reaction and Western blots on nine oral squamous cell carcinoma (OSCC)-derived cell lines and normal oral keratinocytes (NOKs), HDAC6 mRNA and protein expression were commonly upregulated in all cell lines compared with the NOKs. Immunofluorescence analysis detected HDAC6 protein in the cytoplasm of OSCC cell lines. Similar to OSCC cell lines, high frequencies of HDAC6 up-regulation were evident in both mRNA (74%) and protein (51%) levels of primary human OSCC tumors. Among the clinical variables analyzed, the clinical tumor stage was found to be associated with the HDAC6 expression states. The analysis indicated a significant difference in the HDAC6 expression level between the early stage (stage I and II) and advanced-stage (stage III and IV) tumors (P=0.014). These results suggest that HDAC6 expression may be correlated with tumor aggressiveness and offer clues to the planning of new treatments (Sakuma, T., 2006, Int. J. Oncol., 29: 117-124). It was reported recently that HDAC6 rescues neurodegeneration and provides a crucial link between two protein degradation pathways (Pandey U. B., et al, 2007, *Nature* 447 (14):859-863).

Class IIa HDAC includes HDAC 4, 5, and 7. During the past few years, research has established some important biological functions of class IIa in vivo. Strikingly, all these seemingly unrelated processes share the common characteristic of depending on the tight control of MEF2 transcriptional activity by class IIa HDACs. The fact that key processes such as formation of skeletal muscle, cardiac hypertrophy, bone development, T-cell differentiation and neuronal survival are controlled by class IIa HDACs suggests possibilities for therapeutic intervention in numerous human pathologies. That may include several vascular diseases such as arteriosclerosis, stroke and aneurysms as well as tumoral angiogenesis and metastasis, dwarfism and skeletal abnormalities, autoimmune and lympho-proliferative syndromes, and neurodegenerative disorder and cardiac hypertrophy (review see Martin M. et al, 2007, *Oncogene* 26: 5450-5467).

Epigenetic silencing of functional chromosomes by HDAC is one of major mechanisms occurred in many pathological processes, in which functionally critical genes are repressed or reprogrammed by HDAC activities leading to the loss of phenotypes in terminal differentiation, maturation and growth control, and the loss of functionality of tissues. For example, tumor suppressor genes are often silenced during development of cancer and chemical inhibitor of HDAC can derepressed the expression of these tumor suppressor genes, leading to growth arrest and differentiation (Glaros S et al., 2007, *Oncogene* June 4 Epub ahead of print; Mai, A, et al., 2007, *Int J. Biochem Cell Bio., April* 4, Epub ahead of print; Vincent A. et al., 2007, Oncogene, April 30, Epub ahead of print; our unpublished results); and repression of structural genes such as FXN in Friedreich's ataxia and SMN in spinal muscular atrophy can be reversed by HDAC inhibitors that lead to re-expression of FXN and SMN genes and resume the functions in the tissues (Herman D et al., 2006, *Nature Chemical Biology,* 2(10):551-8; Avila AM et al., 2007, *J Clinic Investigation,* 117(3)659-71; de Bore J, 2006, *Tissue Eng.* 12(10):2927-37); Induction of entire MHC II family gene expression through reprogramming of HDAC "hot spot" in chromosome 6p21-22 by HDAC inhibitor further extend epigenetic modulation of immune recognition and immune response (Gialitakis M et al., 2007, *Nucleic Acids Res.,* 34(1); 765-72).

Several classes of HDAC inhibitors have been identified, including (1) short-chain fatty acids, e.g. butyrate and phenylbutyrate; (2) organic hydroxamic acids, e.g. suberoylanilide hydroxamic acid (SAHA) and trichostatin A (TSA); (3) cyclic tetrapeptides containing a 2-amino-8-oxo 9,10-expoxydecanoyl (AOE) moiety, e.g. trapoxin and HC-toxin; (4) cyclic peptides without the AOE moiety, e.g. apicidin and FK228; and (5) benzamides, e.g. MS-275 (EP0847992A1, US2002/0103192A1, WO02/26696A1, WO01/70675A2, WO01/18171A2). Although, HDAC has shown very promising biological roles as a drug target, the success of SAHA from Merck is currently only limited to the treatment of cutaneous T cell lymphoma whereas no major solid tumors yet been reported to be highly effective by this treatment. SAHA and other HDAC inhibitors currently in clinic development are broadly active in inhibition of most if not all of HDAC isoforms or subtypes, thus inheriting from such a pan-inhibition are a broader toxicity profile with current available inhibitors. Therefore, there is still a need and space to discover new compounds with selectivity towards different HDAC isoform or subtype, and therapeutic spectrum against several different human pathologies with improved profile such as more potent HDAC inhibitory activity, more selective action of inhibition on different subtype of HDAC, selective efficacy against one of several human pathologies, and lower toxicity.

SUMMARY OF THE INVENTION

The present invention is directed to certain 2-indolinone derivatives which exhibit selective histone deacetylase inhibition activity and are therefore useful in treating diseases associated with aberrant histone deacetylase activities, such as Rubinstein-Taybi syndrome, fragile X syndrome, leukemia, cancer, immunological disorder, cardiac hypertrophy, bone disorder, and various neurological and neurodegenerative disorders.

DETAILED DESCRIPTION OF THE INVENTION

Various publications are cited throughout the present application. The contents of these publications and contents of documents cited in these publications are herein incorporated herein by reference.

Accordingly, the present invention provides a compound having the structure represented by formula (I), or its stereoisomer, enantiomer, diastereomer, hydrate, or pharmaceutically acceptable salts thereof:

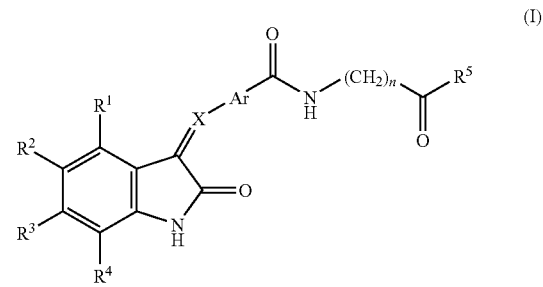

Wherein
X is =CH— or =N—N=CH—;
$R^1$, $R^2$, $R^3$ and $R^4$ are independently hydrogen, halo, alkyl, alkoxy, nitro or trifluoromethyl;
Ar is a benzene ring wherein X is =CH— or =N—N=CH—, or 2,4-dimethyl-1H-pyrrole wherein X is =N—N=CH—;
$R^5$ is —NHOH or

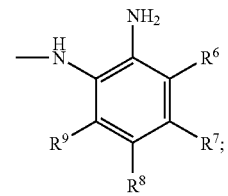

$R^6$, $R^7$, $R^8$ and $R^9$ are independently hydrogen, halo, alkyl, alkoxy or trifluoromethyl;
n is an integer ranging from 1 to 7.

In the above structural formula (I) and throughout the present specification, the following terms have the indicated meaning:

The term "halo" as used herein means fluorine, chlorine, bromine or iodine.

The term "alkyl" as used herein includes methyl, ethyl, n-propyl, iso-propyl, butyl, iso-butyl, sec-butyl, tert-butyl and the like.

The term "alkoxy" as used herein includes methoxy, ethoxy, n-propoxy, isopropoxy, n-butoxy, isobutoxy and the like.

The compounds of this invention are prepared as described below:

(a) Compound 1 is condensed with compound 2 to give compound 3;

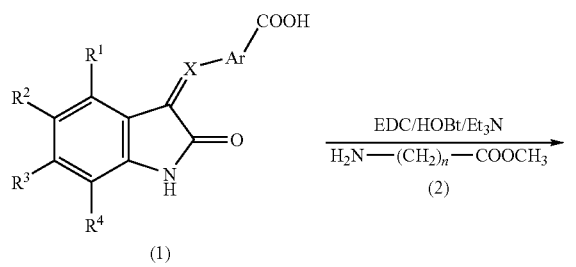

(b) Compound 3 is hydrolyzed to give compound 4;

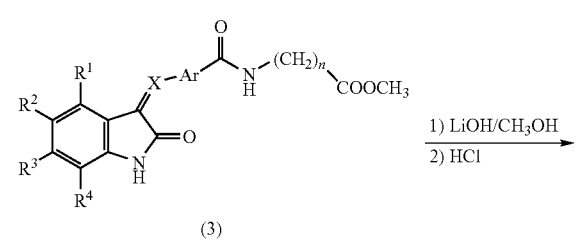

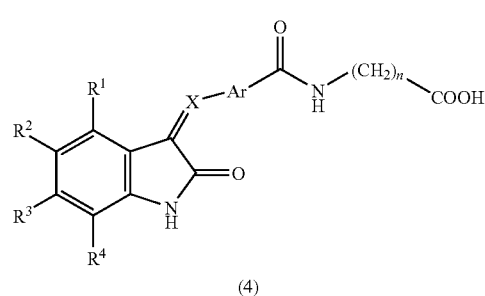

(c) Compound 4 is condensed with hydroxylamine to give compound 5a;

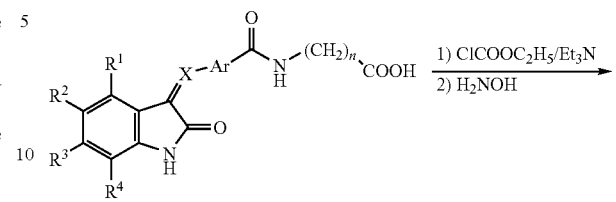

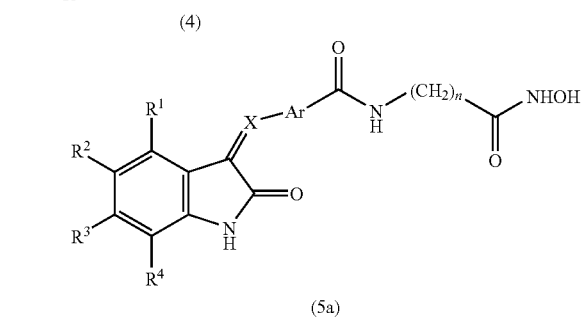

(d) Compound 4 is condensed with compound 6 to give compound 5b.

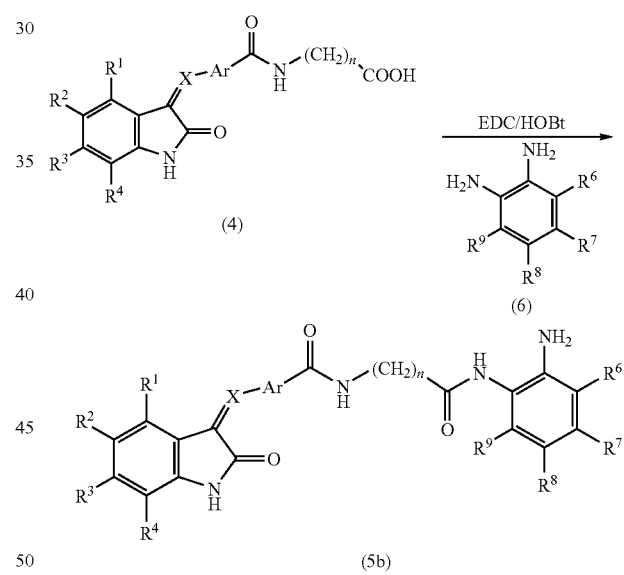

The condensation reaction (a) and (d) are conducted by using a peptide condensing agent such as 1-ethyl-3-(3-dimethylaminopropyl)carbodiimide (EDC), dicyclohexylcarbodiimide (DCC), N,N'-carbonyldiimidazole (CDI), etc. The reaction may be conducted at 0 to 80° C. for 4 to 72 hours. Solvents which may be used are normal solvents such as benzene, toluene, tetrahydrofuran, dioxane, dichloromethane, chloroform, N, N-dimethylformamide, etc. If necessary, a base such as sodium hydroxide, triethylamine and pyridine may be added to the reaction system.

The condensation reaction (c) is conducted by using ClCOOEt as a condensing agent. The reaction may be conducted at 0 to 80° C. for 1 to 24 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

The hydrolysis reaction (b) is conducted by using a hydrolysis agent such as lithium hydroxide, sodium hydroxide, potassium hydroxide, etc. The reaction may be conducted at 0 to 80° C. for 2 to 72 hours. Solvents which may be used are normal solvents such as water, methanol, ethanol, tetrahydrofuran, dioxane, N,N-dimethylformamide, etc. The compounds represented by formula (I) and the intermediate (3) and (4) may be purified or isolated by the conventional separation method such as extraction, recrystallization, column chromatography and the like.

The compounds represented by formula (I) are capable of inhibiting histone deacetylases and are therefore useful in treating diseases associated with abnormal histone deacetylase activities. In particular, they are highly effective against Rubinstein-Taybi syndrome, fragile X syndrome, leukemia, cancer, immunological disorder, cardiac hypertrophy, bone disorder, and various neurological and neurodegenerative disorders.

The compounds represented by formula (I) useful as a drug may be used in the form of a general pharmaceutical composition. The pharmaceutical composition may be in the forms normally employed, such as tablets, capsules, powders, syrups, solutions, suspensions, aerosols, and the like, may contain flavourants, sweeteners etc. in suitable solids or liquid carriers or diluents, or in suitable sterile media to form injectable solutions or suspensions. Such composition typically contains from 0.5 to 70%, preferably 1 to 20% by weight of active compound, the remainder of the composition being pharmaceutically acceptable carriers, diluents or solvents or salt solutions.

The compounds represented by formula (I) are clinically administered to mammals, including man and animals, via oral, nasal, transdermal, pulmonary, or parenteral routes. Administration by the oral route is preferred, being more convenient and avoiding the possible pain and irritation of injection. By either route, the dosage is in the range of about 0.0001 to 200 mg/kg body weight per day administered singly or as a divided dose. However, the optimal dosage for the individual subject being treated will be determined by the person responsible for treatment, generally smaller dose being administered initially and thereafter increments made to determine the most suitable dosage.

Representative compounds of the present invention are shown in Table 1 below. The compound numbers correspond to the "Example numbers" in the Examples section. That is, the synthesis of compound 1 as shown in the Table 1 is described in "Example 1" and the synthesis of compound 52 as shown in the Table 1 is described in "Example 52". The compounds presented in the Table 1 are exemplary only and are not to be construed as limiting the scope of this invention in any manner.

TABLE 1

| Example | Structure | Name |
| --- | --- | --- |
| 3 | 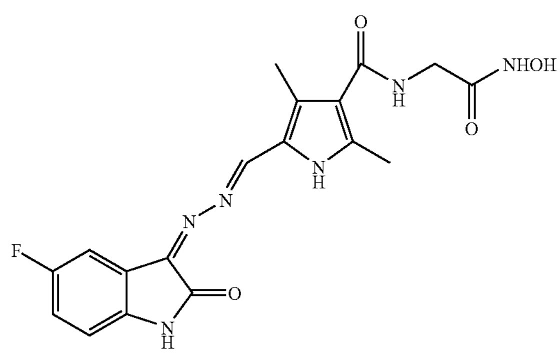 | 2-(5-(((5-fluoro-2-oxoindolin-3-ylidene)hydrazono)methyl)-2,4-dimethyl-1H-pyrrole-3-carboxamido)-N-hydroxyacetamide |
| 4 | 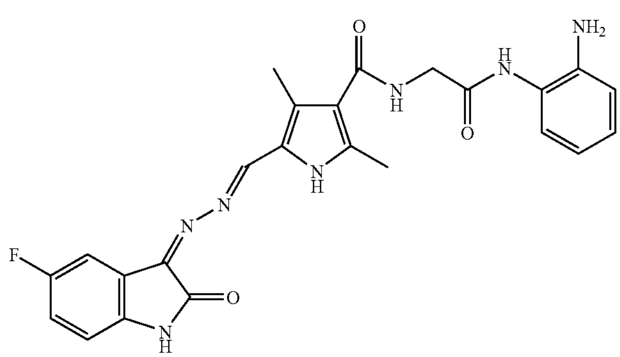 | 2-(5-(((5-fluoro-2-oxoindolin-3-ylidene)hydrazono)methyl)-2,4-dimethyl-1H-pyrrole-3-carboxamido)-N-(2-aminophenyl)acetamide |

TABLE 1-continued

| Example | Structure | Name |
|---|---|---|
| 7 | 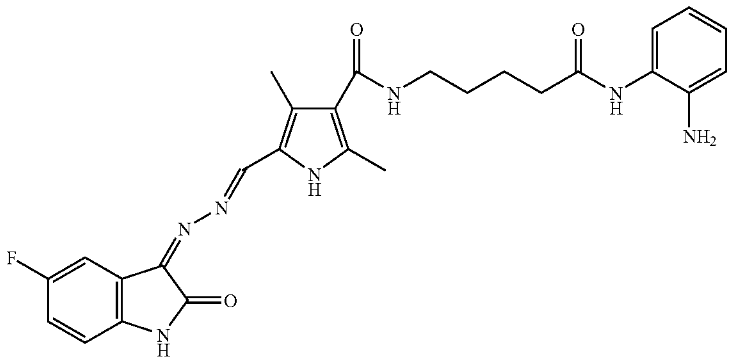 | 5-(5-(((5-fluoro-2-oxoindolin-3-ylidene)hydrazono)methyl)-2,4-dimethyl-1H-pyrrole-3-carboxamido)-N-(2-aminophenyl)pentanamide |
| 8 | 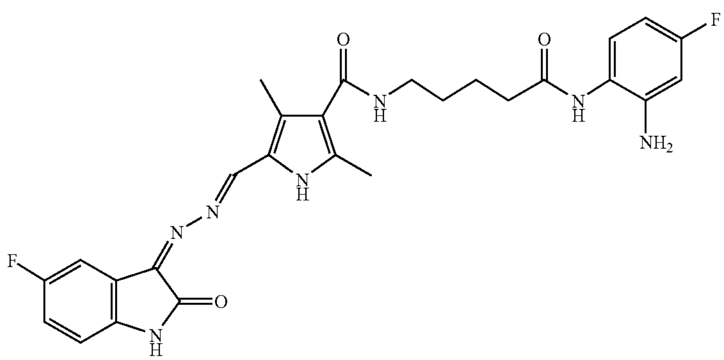 | 5-(5-(((5-fluoro-2-oxoindolin-3-ylidene)hydrazono)methyl)-2,4-dimethyl-1H-pyrrole-3-carboxamido)-N-(2-amino-4-fluorophenyl)-pentanamide |
| 11 | 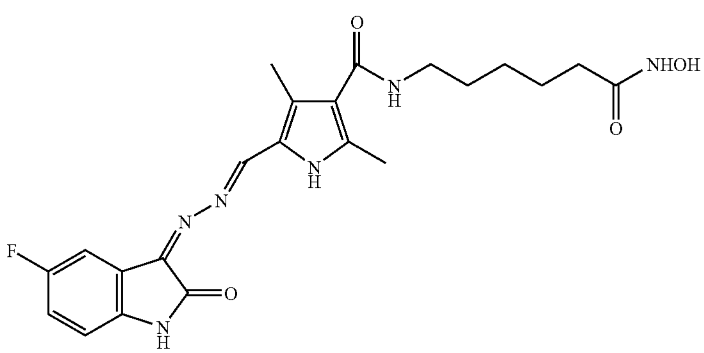 | 6-(5-(((5-fluoro-2-oxoindolin-3-ylidene)hydrazono)methyl)-2,4-dimethyl-1H-pyrrole-3-carboxamido)-N-hydroxyhexanamide |
| 12 | 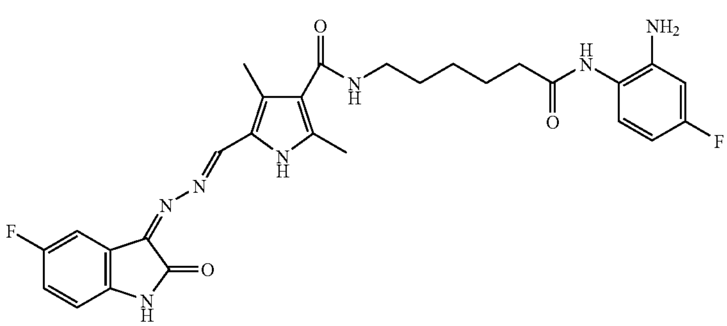 | 6-(5-(((5-fluoro-2-oxoindolin-3-ylidene)hydrazono)methyl)-2,4-dimethyl-1H-pyrrole-3-carboxamido)-N-(2-amino-4-fluorophenyl)-hexanamide |

TABLE 1-continued

| Example | Structure | Name |
|---|---|---|
| 13 | 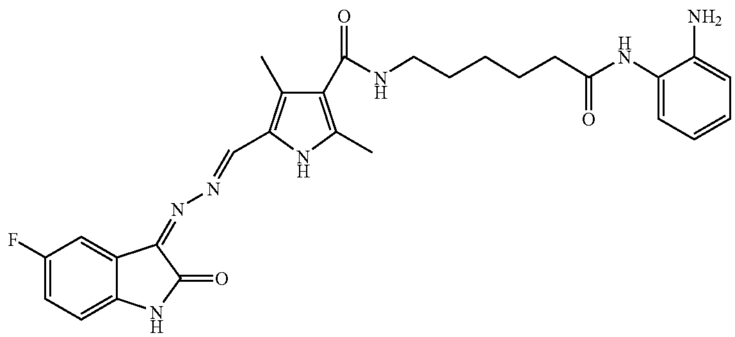 | 6-(5-(((5-fluoro-2-oxoindolin-3-ylidene)hydrazono)methyl)-2,4-dimethyl-1H-pyrrole-3-carboxamido)-N-(2-aminophenyl)hexanamide |
| 14 | 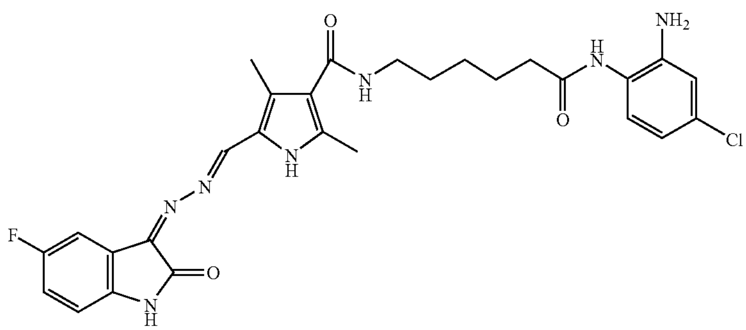 | 6-(5-(((5-fluoro-2-oxoindolin-3-ylidene)hydrazono)methyl)-2,4-dimethyl-1H-pyrrole-3-carboxamido)-N-(2-amino-4-chlorophenyl)hexanamide |
| 15 | 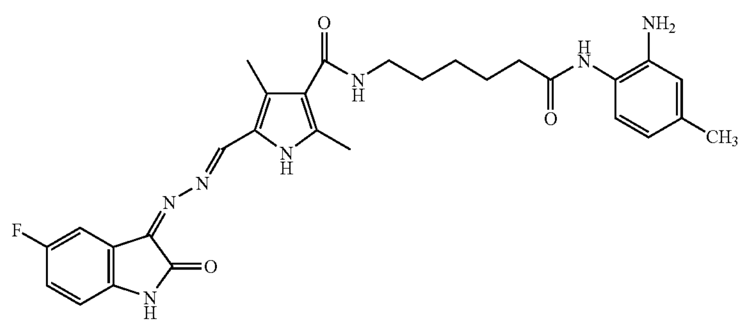 | 6-(5-(((5-fluoro-2-oxoindolin-3-ylidene)hydrazono)methyl)-2,4-dimethyl-1H-pyrrole-3-carboxamido)-N-(2-amino-4-methylphenyl)hexanamide |
| 16 | 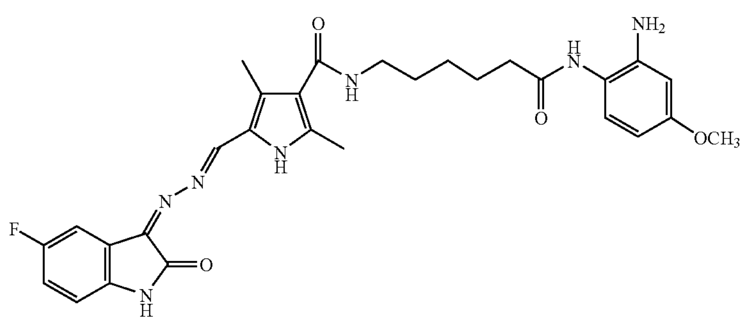 | 6-(5-(((5-fluoro-2-oxoindolin-3-ylidene)hydrazono)methyl)-2,4-dimethyl-1H-pyrrole-3-carboxamido)-N-(2-amino-4-methoxyphenyl)hexanamide |

TABLE 1-continued

| Example | Structure | Name |
|---|---|---|
| 17 | 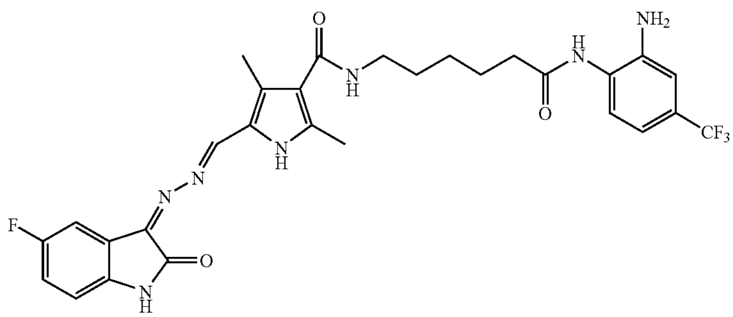 | 6-(5-(((5-fluoro-2-oxoindolin-3-ylidene)hydrazono)methyl)-2,4-dimethyl-1H-pyrrole-3-carboxamido)-N-(2-amino-4-trifluoromethylphenyl)hexanamide |
| 18 | 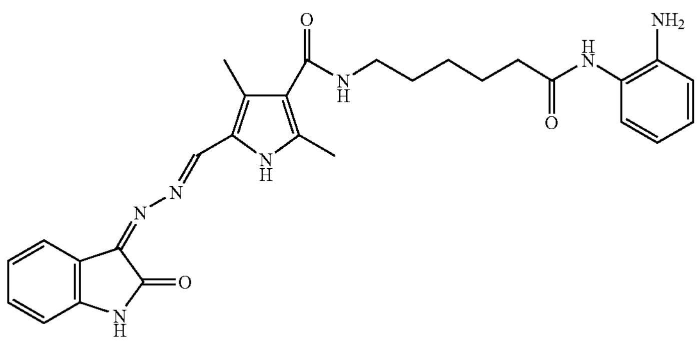 | 6-(5-(((2-oxoindolin-3-ylidene)hydrazono)methyl)-2,4-dimethyl-1H-pyrrole-3-carboxamido)-N-(2-aminophenyl)hexanamide |
| 19 | 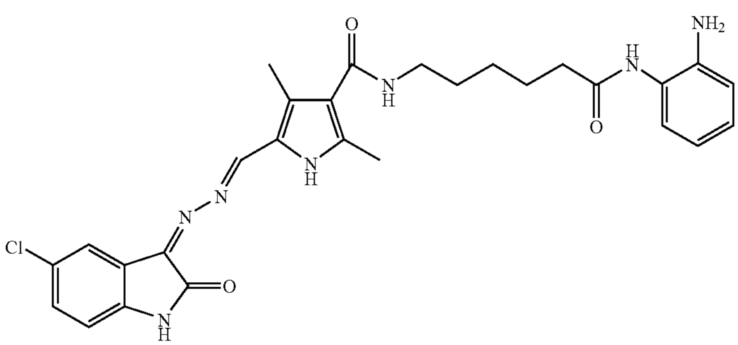 | 6-(5-(((5-chloro-2-oxoindolin-3-ylidene)hydrazono)methyl)-2,4-dimethyl-1H-pyrrole-3-carboxamido)-N-(2-aminophenyl)hexanamide |
| 20 | 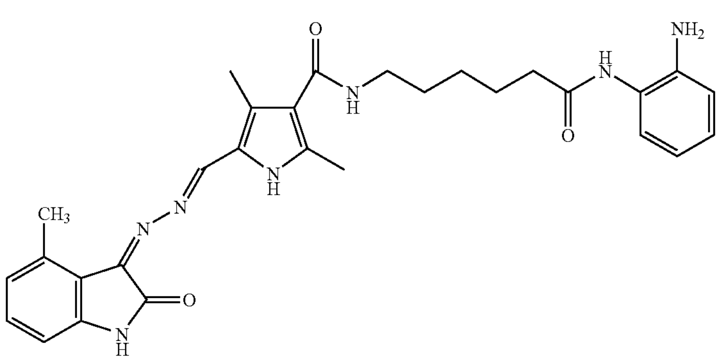 | 6-(5-(((4-methyl-2-oxoindolin-3-ylidene)hydrazono)methyl)-2,4-dimethyl-1H-pyrrole-3-carboxamido)-N-(2-aminophenyl)hexanamide |

TABLE 1-continued

| Example | Structure | Name |
|---|---|---|
| 21 | 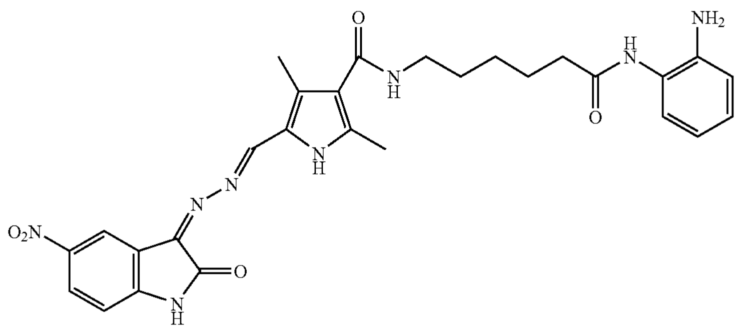 | 6-(5-(((5-nitro-2-oxoindolin-3-ylidene)hydrazono)methyl)-2,4-dimethyl-1H-pyrrole-3-carboxamido)-N-(2-aminophenyl)hexanamide |
| 22 | 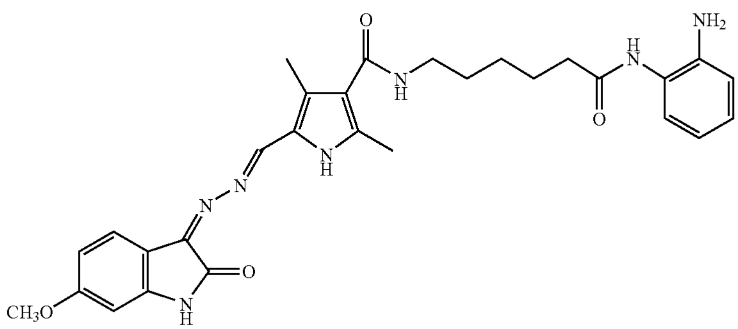 | 6-(5-(((6-methoxy-2-oxoindolin-3-ylidene)hydrazono)methyl)-2,4-dimethyl-1H-pyrrole-3-carboxamido)-N-(2-aminophenyl)hexanamide |
| 23 | 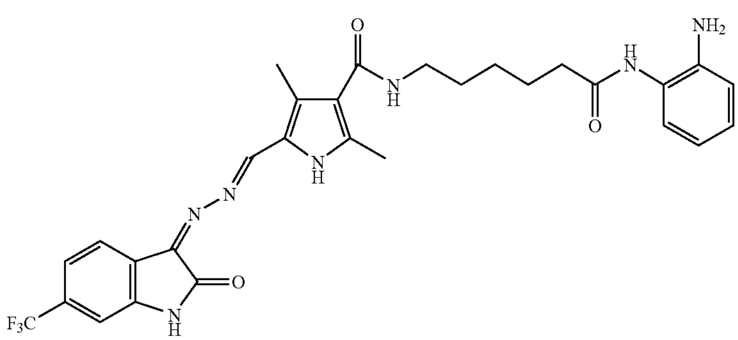 | 6-(5-(((6-trifluoromethyl-2-oxoindolin-3-ylidene)hydrazono)methyl)-2,4-di-methyl-1H-pyrrole-3-carboxamido)-N-(2-aminophenyl)-hexanamide |
| 26 | 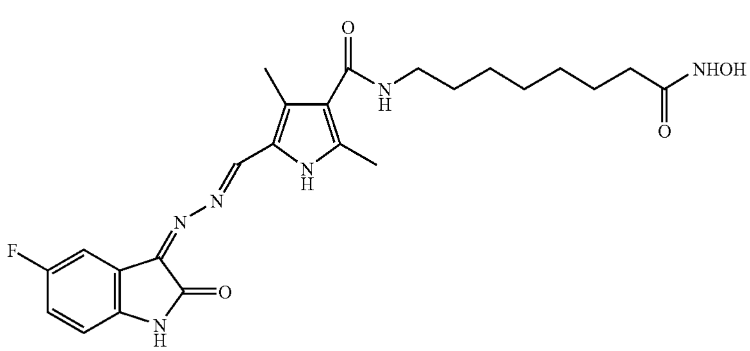 | 8-(5-(((5-fluoro-2-oxoindolin-3-ylidene)hydrazono)methyl)-2,4-dimethyl-1H-pyrrole-3-carboxamido)-N-hydroxyoctanamide |

TABLE 1-continued

| Example | Structure | Name |
|---|---|---|
| 27 | 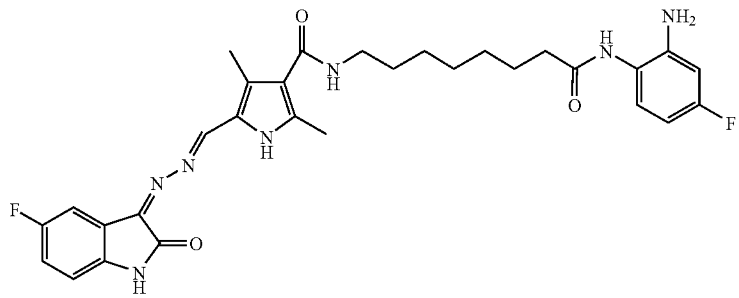 | 8-(5-(((5-fluoro-2-oxoindolin-3-ylidene)hydrazono)methyl)-2,4-dimethyl-1H-pyrrole-3-carboxamido)-N-(2-amino4-fluorophenyl)-octanamide |
| 28 | 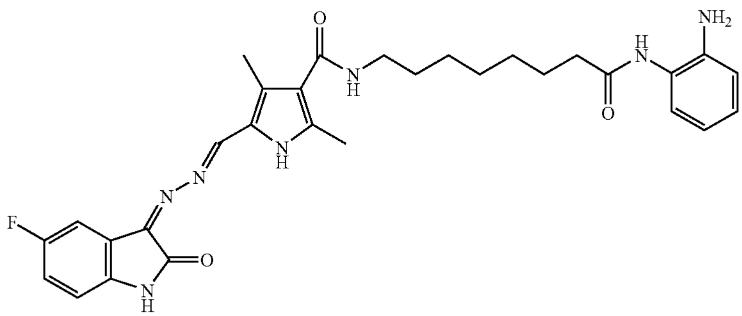 | 8-(5-(((5-fluoro-2-oxoindolin-3-ylidene)hydrazono)methyl)-2,4-dimethyl-1H-pyrrole-3-carboxamido)-N-(2-aminophenyl)octanamide |
| 31 | 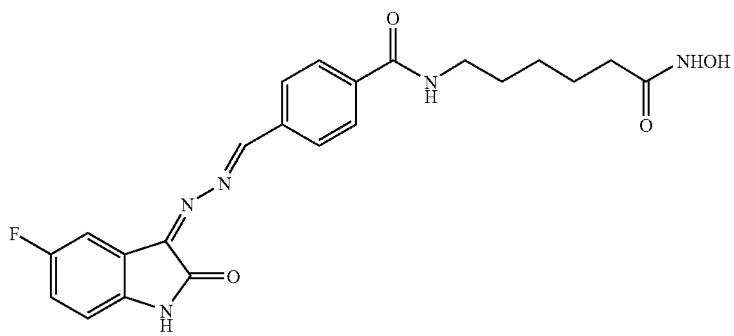 | 6-(4-(((5-fluoro-2-oxoindolin-3-ylidene)hydrazono)methyl)-benzamido)-N-hydroxyhexanamide |
| 32 | 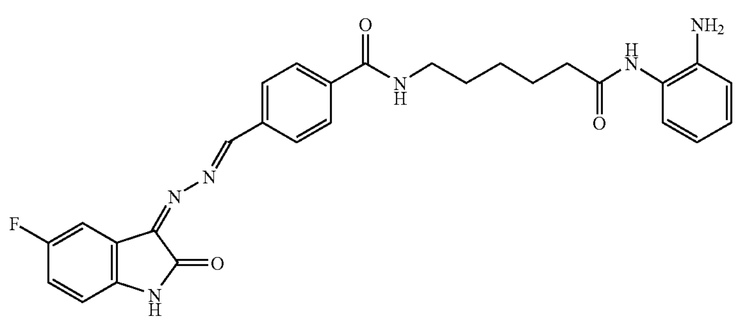 | 6-(4-(((5-fluoro-2-oxoindolin-3-ylidene)hydrazono)methyl)-benzamido)-N-(2-aminophenyl)-hexanamide |
| 35 | 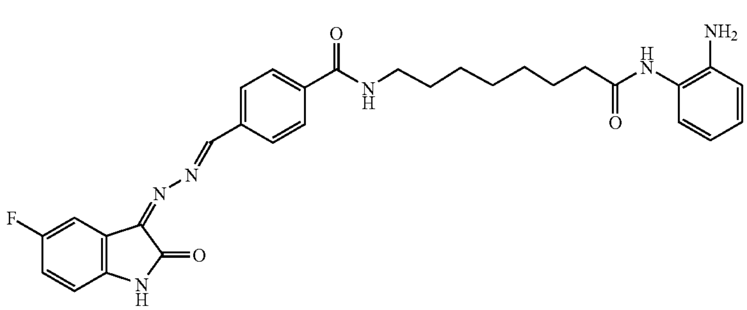 | 8-(4-(((5-fluoro-2-oxoindolin-3-ylidene)hydrazono)methyl)-benzamido)-N-(2-aminophenyl)-octanamide |

TABLE 1-continued

| Example | Structure | Name |
|---|---|---|
| 36 | 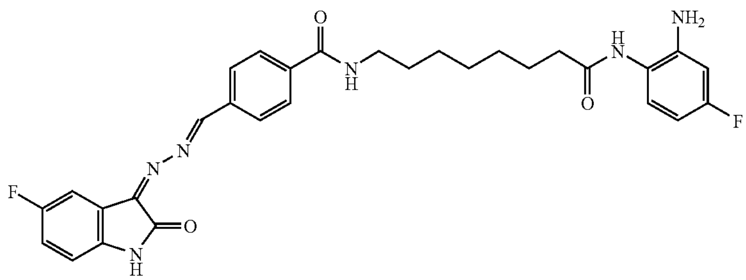 | 8-(4-(((5-fluoro-2-oxoindolin-3-ylidene)hydrazono)methyl)-benzamido)-N-(2-amino-4-fluorophenyl)octanamide |
| 39 | 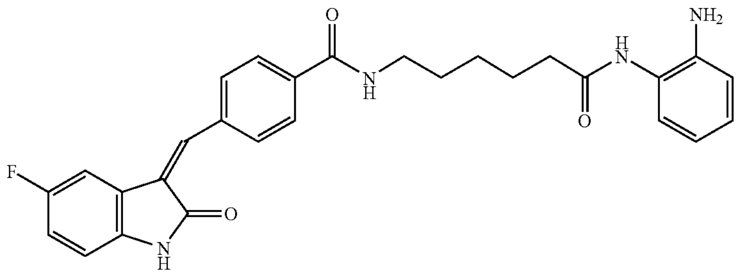 | 6-(4-(((5-fluoro-2-oxoindolin-3-ylidene)methyl)benzamido)-N-(2-aminophenyl)hexanamide |
| 40 | 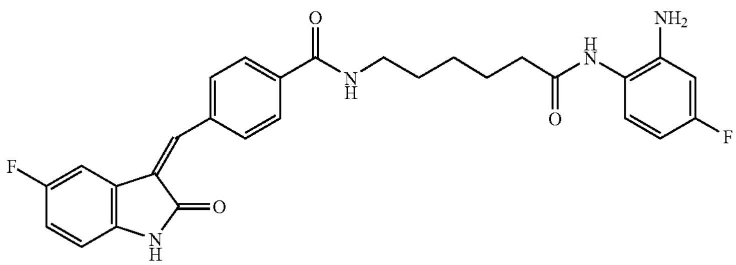 | 6-(4-((5-fluoro-2-oxoindolin-3-ylidene)methyl)benzamido)-N-(2-amino-4-fluorophenyl)-hexanamide |
| 41 | 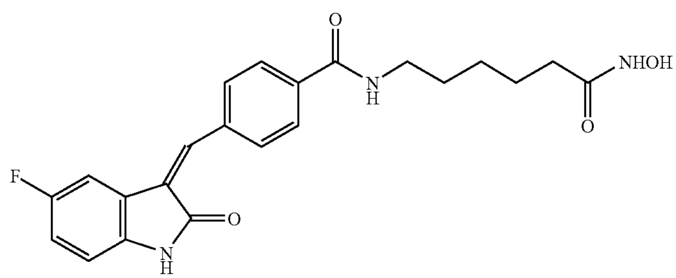 | 6-(4-((5-fluoro-2-oxoindolin-3-ylidene)methyl)benzamido)-N-hydroxyhexanamide |
| 44 | 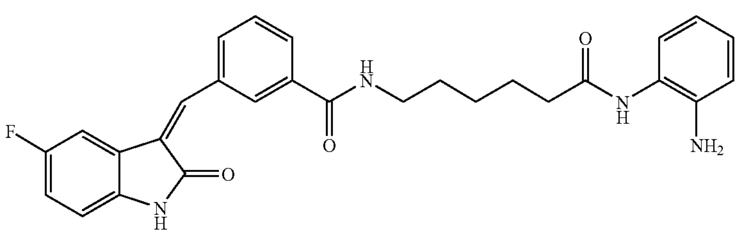 | 6-(3-(((5-fluoro-2-oxoindolin-3-ylidene)methyl)benzamido)-N-(2-aminophenyl)hexanamide |
| 45 | 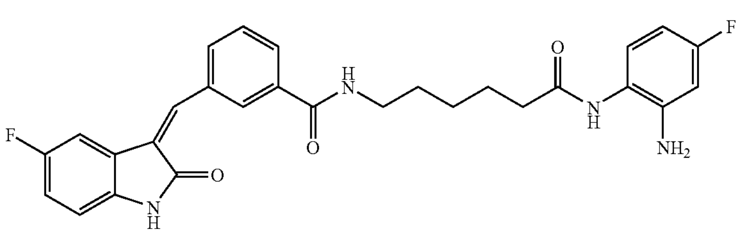 | 6-(3-(((5-fluoro-2-oxoindolin-3-ylidene)methyl)benzamido)-N-(2-amino-4-fluorophenyl)-hexanamide |

TABLE 1-continued

| Example | Structure | Name |
| --- | --- | --- |
| 46 | 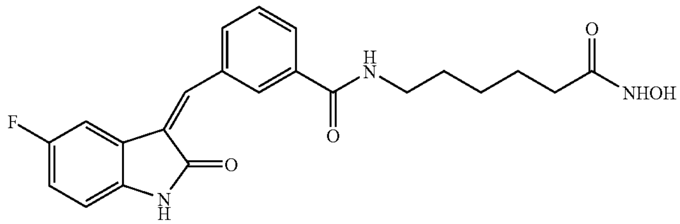 | 6-(3-((5-fluoro-2-oxoindolin-3-ylidene)methyl)benzamido)-N-hydroxyhexanamide |
| 49 | 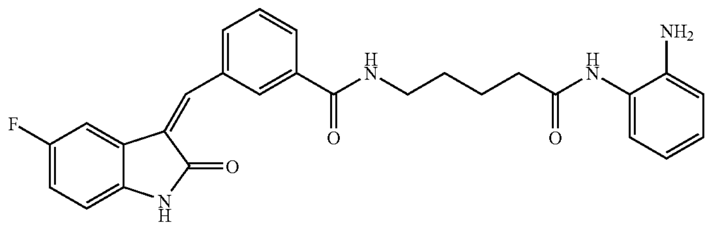 | 5-(3-((5-fluoro-2-oxoindolin-3-ylidene)methyl)benzamido)-N-(2-aminophenyl)pentanamide |
| 50 | 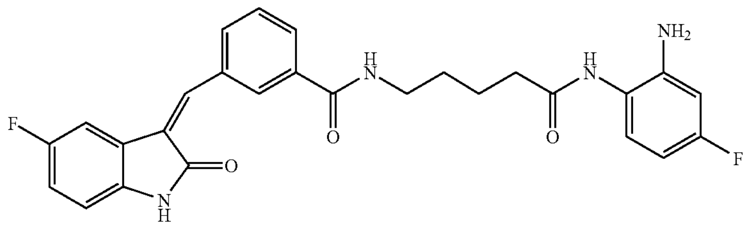 | 5-(3-((5-fluoro-2-oxoindolin-3-ylidene)methyl)benzamido)-N-(2-amino-4-fluorophenyl)-pentanamide |
| 51 | 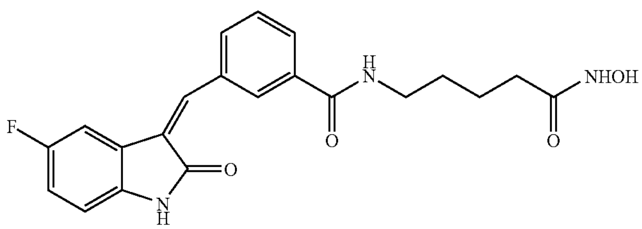 | 5-(3-((5-fluoro-2-oxoindolin-3-ylidene)methyl)benzamido)-N-hydroxypentanamide |
| 54 | 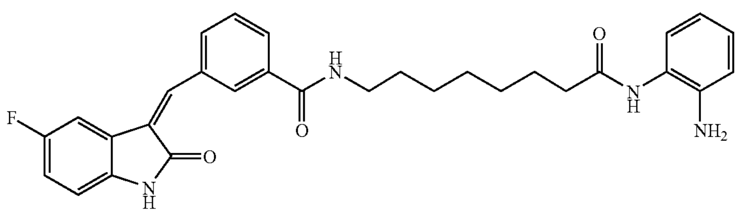 | 8-(3-((5-fluoro-2-oxoindolin-3-ylidene)methyl)benzamido)-N-(2-aminophenyl)octanamide |
| 55 | 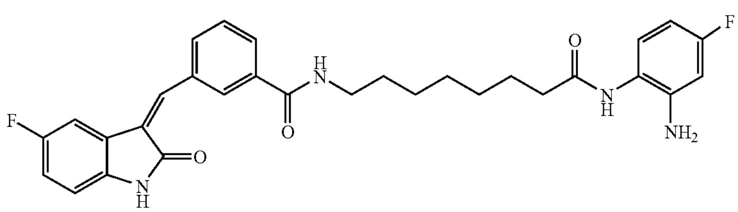 | 8-(3-((5-fluoro-2-oxoindolin-3-ylidene)methyl)benzamido)-N-(2-amino-4-fluorophenyl)-octanamide |
| 56 | 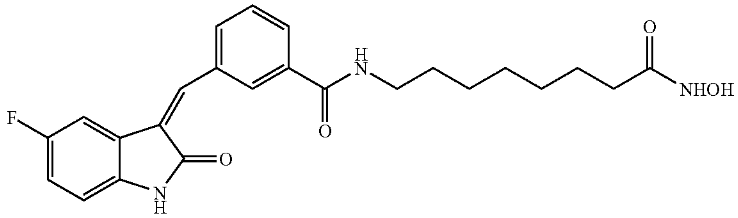 | 8-(3-((5-fluoro-2-oxoindolin-3-ylidene)methyl)benzamido)-N-hydroxyoctanamide |

Further, all parts and percentages in the examples, as well as in the remainder of the specification, are by weight unless otherwise specified. Any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of 2-(5-(((5-fluoro-2-oxoindolin-3-ylidene)hydrazono)methyl)-2,4-dimethyl-1H-pyrrole-3-carboxamido)-acetic acid methyl ester

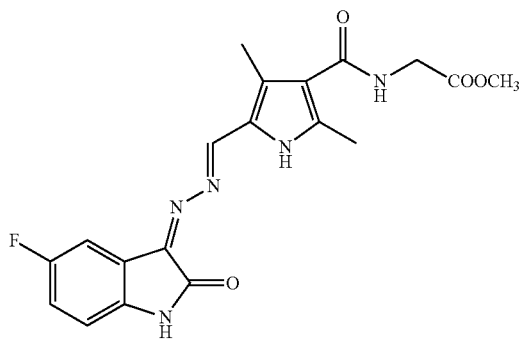

5-(((5-fluoro-2-oxoindolin-3-ylidene)hydrazono)methyl)-2,4-dimethyl-1H-pyrrole-3-carboxylic acid (328 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and glycine methyl ester hydrochloride (151.8 mg, 1.2 mmol) were added. The mixture was stirred for 24 hours at room temperature. The mixture was diluted with 400 mL of brine. The solids were collected by vacuum filtration, washed with water and dried under vacuum to give the title compound (244 mg, 61% yield) as a red solid. LC-MS (m/z) 400 (M+1).

EXAMPLE 2

Preparation of 2-(5-(((5-fluoro-2-oxoindolin-3-ylidene)hydrazono)methyl)-2,4-dimethyl-1H-pyrrole-3-carboxamido)-acetic acid

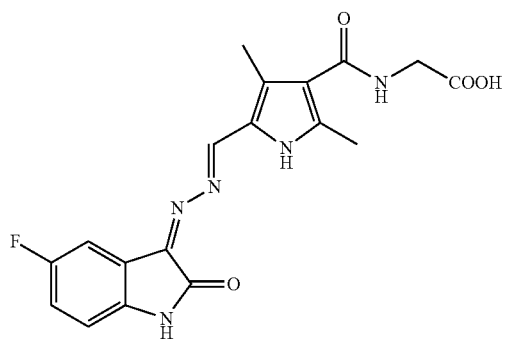

2-(5-(((5-fluoro-2-oxoindolin-3-ylidene)hydrazono)methyl)-2,4-dimethyl-1H-pyrrole-3-carboxamido)-acetic acid methyl ester (399 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (128 mg, 33% yield) as a red solid. LC-MS (m/z) 386 (M+1).

EXAMPLE 3

Preparation of 2-(5-(((5-fluoro-2-oxoindolin-3-ylidene)hydrazono)methyl)-2,4-dimethyl-1H-pyrrole-3-carboxamido)-N-hydroxyacetamide

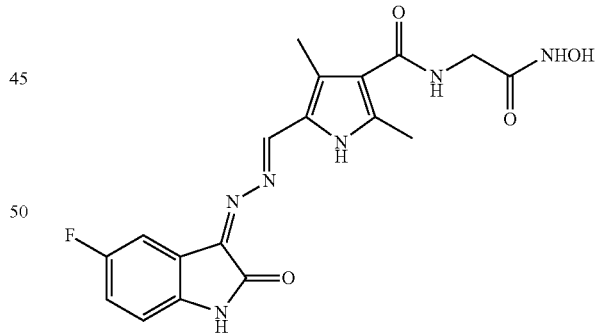

2-(5-(((5-fluoro-2-oxoindolin-3-ylidene)hydrazono)methyl)-2,4-dimethyl-1H-pyrrole-3-carboxamido)-acetic acid (385 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (140 mg, 35%) as a red solid. LC-MS (m/z) 401 (M+1).

EXAMPLE 4

Preparation of 2-(5-(((5-fluoro-2-oxoindolin-3-ylidene)hydrazono)methyl)-2,4-dimethyl-1H-pyrrole-3-carboxamido)-N-(2-aminophenyl)acetamide

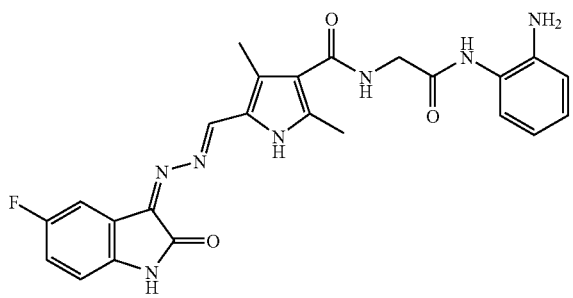

2-(5-(((5-fluoro-2-oxoindolin-3-ylidene)hydrazono)methyl)-2,4-dimethyl-1H-pyrrole-3-carboxamido)-acetic acid (385 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (342 mg, 72% yield) as a red solid. LC-MS (m/z) 476 (M+1).

EXAMPLE 5

Preparation of 5-(5-(((5-fluoro-2-oxoindolin-3-ylidene)hydrazono)methyl)-2,4-dimethyl-1H-pyrrole-3-carboxamido)-pentanoic acid methyl ester

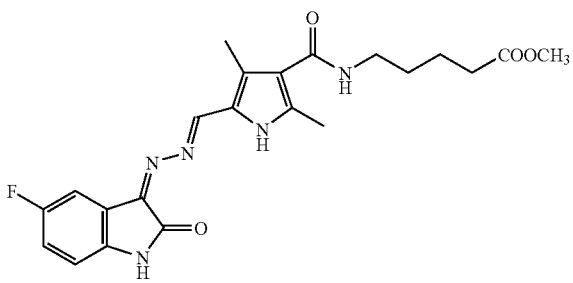

5-(((5-fluoro-2-oxoindolin-3-ylidene)hydrazono)methyl)-2,4-dimethyl-1H-pyrrole-3-carboxylic acid (328 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 5-aminovaleric acid methyl ester hydrochloride (202 mg, 1.2 mmol) were added. The mixture was stirred for 24 hours at room temperature. The mixture was diluted with 400 mL of brine. The solids were collected by vacuum filtration, washed with water and dried under vacuum to give the title compound (300mg, 68% yield) as a red solid. LC-MS (m/z) 442 (M+1).

EXAMPLE 6

Preparation of 5-(5-(((5-fluoro-2-oxoindolin-3-ylidene)hydrazono)methyl)-2,4-dimethyl-1H-pyrrole-3-carboxamido)-pentanoic acid

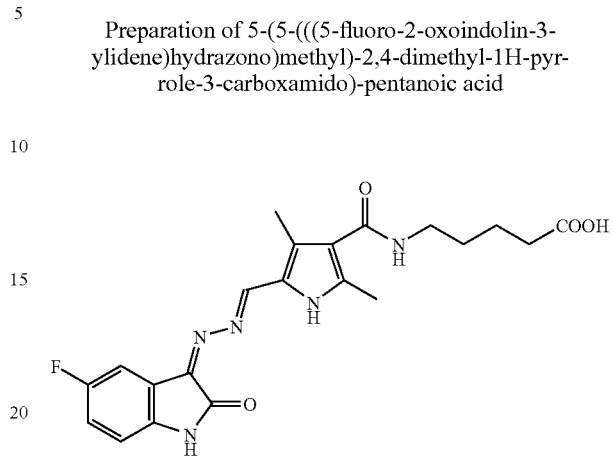

5-(5-(((5-fluoro-2-oxoindolin-3-ylidene)hydrazono)methyl)-2,4-dimethyl-1H-pyrrole-3-carboxamido)-pentanoic acid methyl ester (441 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (167 mg, 39% yield) as a red solid. LC-MS (m/z) 428 (M+1).

EXAMPLE 7

Preparation of 5-(5-(((5-fluoro-2-oxoindolin-3-ylidene)hydrazono)methyl)-2,4-dimethyl-1H-pyrrole-3-carboxamido)-N-(2-aminophenyl)pentanamide

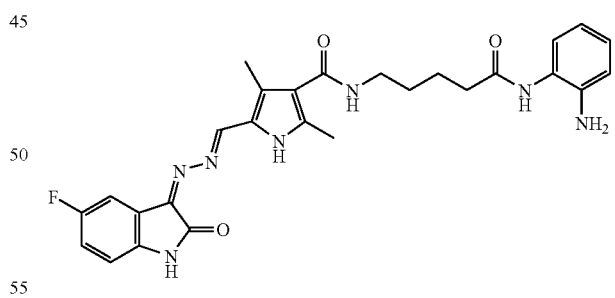

5-(5-(((5-fluoro-2-oxoindolin-3-ylidene)hydrazono)methyl)-2,4-dimethyl-1H-pyrrole-3-carboxamido)-pentanoic acid (427 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (388 mg, 75% yield) as a red solid. LC-MS (m/z) 518 (M+1).

EXAMPLE 8

Preparation of 5-(5-(((5-fluoro-2-oxoindolin-3-ylidene)hydrazono)methyl)-2,4-dimethyl-1H-pyrrole-3-carboxamido)-N-(2-amino-4-fluorophenyl)pentanamide

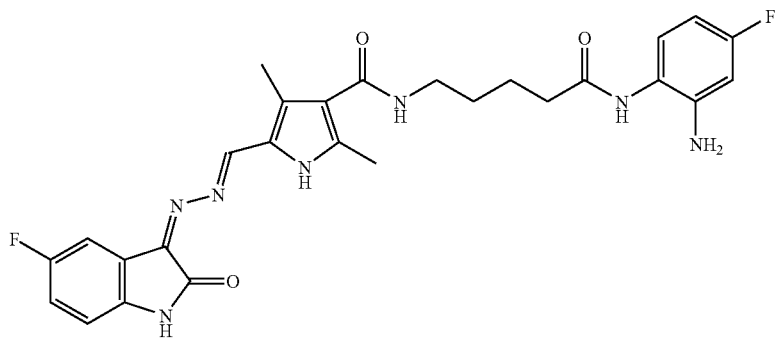

5-(5-(((5-fluoro-2-oxoindolin-3-ylidene)hydrazono)methyl)-2,4-dimethyl-1H-pyrrole-3-carboxamido)-pentanoic acid (427 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (439 mg, 82% yield) as a red solid. LC-MS (m/z) 536 (M+1).

EXAMPLE 9

Preparation of 6-(5-(((5-fluoro-2-oxoindolin-3-ylidene)hydrazono)methyl)-2,4-dimethyl-1H-pyrrole-3-carboxamido)-hexanoic acid methyl ester

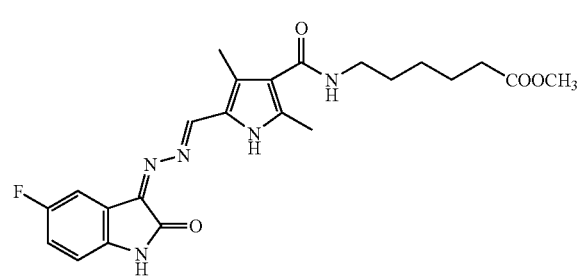

5-(((5-fluoro-2-oxoindolin-3-ylidene)hydrazono)methyl)-2,4-dimethyl-1H-pyrrole-3-carboxylic acid (328 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and brine. The solids were collected by vacuum filtration, washed 6-aminocaproic acid methyl ester hydrochloride (219 mg, 1.2 mmol) were added. The mixture was stirred for 24 hours at room temperature. The mixture was diluted with 400 mL of with water and dried under vacuum to give the title compound (287 mg, 63% yield) as a red solid. LC-MS (m/z) 456 (M+1).

EXAMPLE 10

Preparation of 6-(5-(((5-fluoro-2-oxoindolin-3-ylidene)hydrazono)methyl)-2,4-dimethyl-1H-pyrrole-3-carboxamido)-hexanoic acid

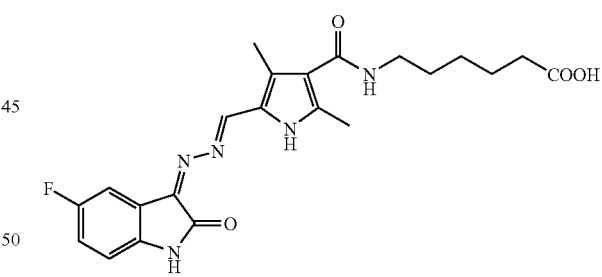

6-(5-(((5-fluoro-2-oxoindolin-3-ylidene)hydrazono)methyl)-2,4-dimethyl-1H-pyrrole-3-carboxamido)-hexanoic acid methyl ester (455 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (163 mg, 37% yield) as a red solid. LC-MS (m/z) 442 (M+1).

EXAMPLE 11

Preparation of 6-(5-(((5-fluoro-2-oxoindolin-3-ylidene)hydrazono)methyl)-2,4-dimethyl-1H-pyrrole-3-carboxamido)-N-hydroxyhexanamide

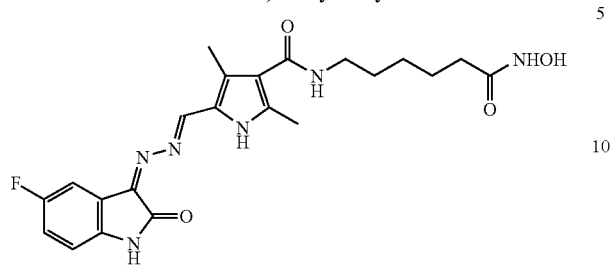

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (201 mg, 44%) as a red solid. LC-MS (m/z) 457 (M+1).

EXAMPLE 12

Preparation of 6-(5-(((5-fluoro-2-oxoindolin-3-ylidene)hydrazono)methyl)-2,4-dimethyl-1H-pyrrole-3-carboxamido)-N-(2-amino-4-fluorophenyl)hexanamide

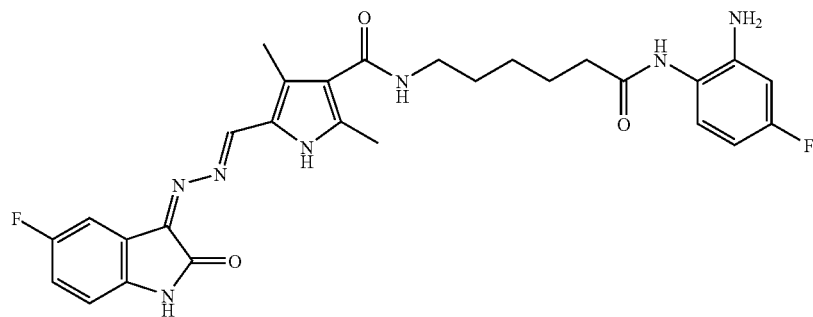

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (417 mg, 76% yield) as a red solid. $^1$H NMR (DMSO-$d_6$)δ1.35 (m, 2H, CH$_2$), 1.53 (m, 2H, CH$_2$), 1.62 (m, 2H, CH$_2$), 2.30 (t, J=8.0 Hz, 2H, CH$_2$CO), 2.33 (s, 3H, pyrrole-CH$_3$), 2.43 (s, 3H, pyrrole-CH$_3$), 3.21 (m, 2H, NCH$_2$), 5.12 (s, 2H, benzene-NH$_2$), 6.28 (m, 1H, Ar—H), 6.47 (dd, J=4.0 and 8.0 Hz, 1H, Ar—H), 6.85 (dd, J=4.0 and 8.0 Hz, 1H, Ar—H), 7.07 (td, J=4.0 and 8.0 Hz, 1H, Ar—H), 7.20 (td, J=4.0 and 8.0 Hz, 1H, Ar—H), 7.64 (t, J=4.0 Hz, CONH), 8.33 (dd, J=4.0 and 8.0 Hz, 1H, Ar—H), 8.63 (s, 1H, vinyl-H), 9.02 (s, 1H, benzene-NH), 10.72 (s, 1H, indolinone-NH), 11.82 (s, 1H, pyrrole-NH). LC-MS (m/z) 550 (M+1).

EXAMPLE 13

Preparation of 6-(5-(((5-fluoro-2-oxoindolin-3-ylidene)hydrazono)methyl)-2,4-dimethyl-1H-pyrrole-3-carboxamido)-N-(2-aminophenyl)hexanamide

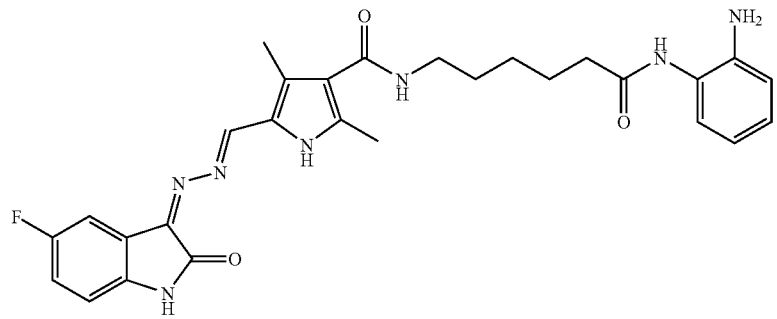

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (430 mg, 81% yield) as a red solid. $^1$H NMR (DMSO-$d_6$) δ 1.38 (m, 2H, $CH_2$), 1.54 (m, 2H, $CH_2$), 1.62 (m, 2H, $CH_2$), 2.30 (s, 3H, pyrrole-$CH_3$), 2.32 (t, J=8.0 Hz, 2H, $CH_2CO$), 2.41 (s, 3H, pyrrole-$CH_3$), 3.22 (m, 2H, $NCH_2$), 4.82 (s, 2H, benzene-$NH_2$), 6.51 (t, J=8.0 Hz, 1H, Ar—H), 6.69 (d, J=8.0 Hz, 1H, Ar—H), 6.87 (m, 2H, Ar—H), 7.14 (d, J=8.0 Hz, 1H, Ar—H), 7.20 (m, 1H, Ar—H), 7.65 (t, J=4.0 Hz, 1H, CONH), 8.33 (dd, J=4.0 and 8.0 Hz, 1H, Ar—H), 8.63 (s, 1H, vinyl-H), 9.11 (s, 1H, benzene-NH), 10.73 (s, 1H, indolinone-NH), 11.82 (s, 1H, pyrrole-NH). LC-MS (m/z) 532 (M+1).

EXAMPLE 14

Preparation of 6-(5-(((5-fluoro-2-oxoindolin-3-ylidene)hydrazono)methyl)-2,4-dimethyl-1H-pyrrole-3-carboxamido)-N-(2-amino-4-chlorophenyl)hexanamide

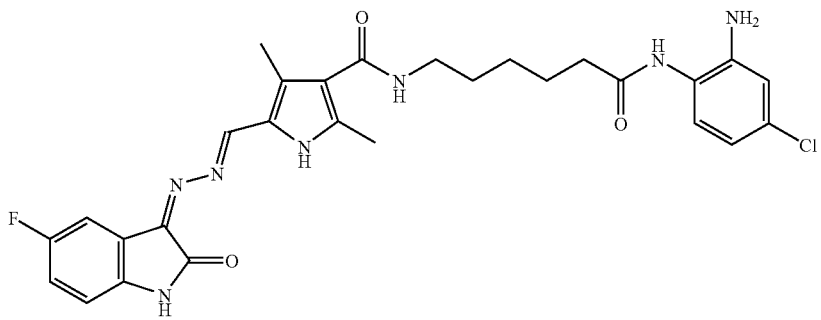

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-chloro-o-phenylenediamine (171 mg, 1.2 mmol) were added. The mixture was stirred for 24 hours at room temperature. The mixture was diluted with 400 mL of brine. The solids were collected by vacuum filtration, washed with water and dried under vacuum to give the title compound (402 mg, 71% yield) as a red solid. LC-MS (m/z) 566 (M+1).

EXAMPLE 15

Preparation of 6-(5-(((5-fluoro-2-oxoindolin-3-ylidene)hydrazono)methyl)-2,4-dimethyl-1H-pyrrole-3-carboxamido)-N-(2-amino-4-methylphenyl)hexanamide

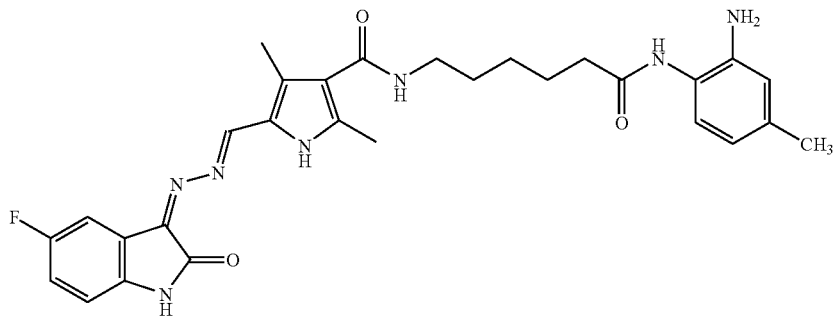

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-methyl-o-phenylenediamine (146 mg, 1.2 mmol) were added. The mixture was stirred for 24 hours at room temperature. The mixture was diluted with 400 mL of brine. The solids were collected by vacuum filtration, washed with water and dried under vacuum to give the title compound (376 mg, 69% yield) as a red solid. LC-MS (m/z) 546 (M+1).

EXAMPLE 16

Preparation of 6-(5-(((5-fluoro-2-oxoindolin-3-ylidene)hydrazono)methyl)-2,4-dimethyl-1H-pyrrole-3-carboxamido)-N-(2-amino-4-methoxyphenyl)hexanamide

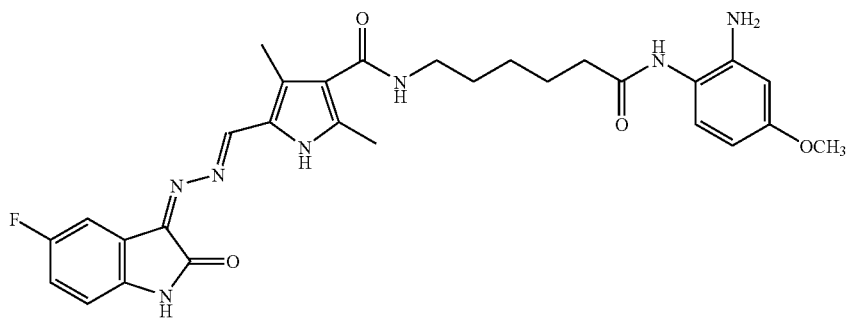

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-methoxy-o-phenylenediamine (166 mg, 1.2 mmol) were added. The mixture was stirred for 24 hours at room temperature. The mixture was diluted with 400 mL of brine. The solids were collected by vacuum filtration, washed with water and dried under vacuum to give the title compound (427 mg, 76% yield) as a red solid. LC-MS (m/z) 562 (M+1).

EXAMPLE 17

Preparation of 6-(5-((((5-fluoro-2-oxoindolin-3-ylidene)hydrazono)methyl)-2,4-dimethyl-1H-pyrrole-3-carboxamido)-N-(2-amino-4-trifluoromethylphenyl)hexanamide

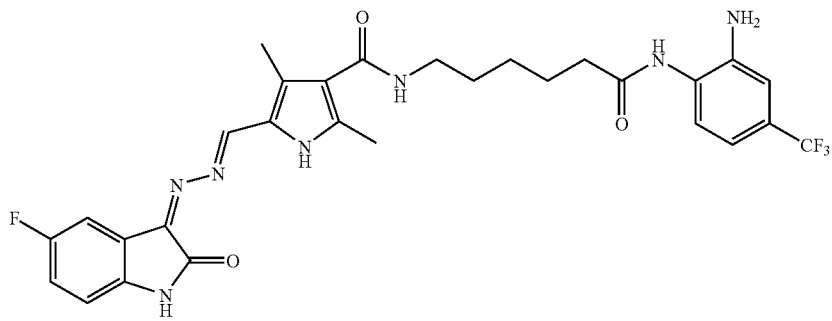

6-(5-(((5-fluoro-2-oxoindolin-3-ylidene)hydrazono)methyl)-2,4-dimethyl-1H-pyrrole-3-carboxamido)-hexanoic acid (441 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-trifluoromethyl-o-phenylenediamine (211 mg, 1.2 mmol) were added. The mixture was stirred for 24 hours at room temperature. The mixture was diluted with 400 mL of brine. The solids were collected by vacuum filtration, washed with water and dried under vacuum to give the title compound (390 mg, 65% yield) as a red solid. LC-MS (m/z) 600 (M+1).

EXAMPLE 18

Preparation of 6-(5-(((2-oxoindolin-3-ylidene)hydrazono)methyl)-2,4-dimethyl-1H-pyrrole-3-carboxamido)-N-(2-aminophenyl)hexanamide

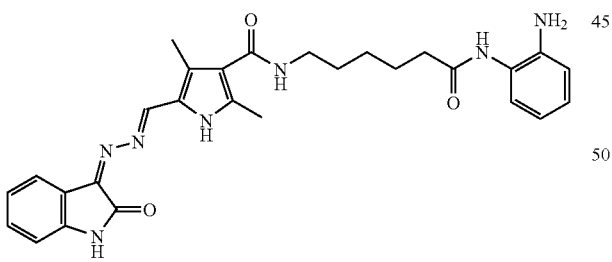

6-(5-(((2-oxoindolin-3-ylidene)hydrazono)methyl)-2,4-dimethyl-1H-pyrrole-3-carboxamido)-hexanoic acid (423 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (395 mg, 77% yield) as a red solid. LC-MS (m/z) 514 (M+1).

EXAMPLE 19

Preparation of 6-(5-((((5-chloro-2-oxoindolin-3-ylidene)hydrazono)methyl)-2,4-dimethyl-1H-pyrrole-3-carboxamido)-N-(2-aminophenyl)hexanamide

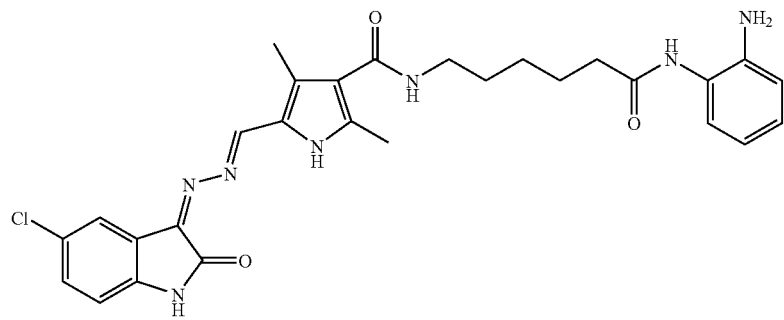

6-(5-(((5-chloro-2-oxoindolin-3-ylidene)hydrazono)methyl)-2,4-dimethyl-1H-pyrrole-3 -carboxamido)-hexanoic acid (458 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (438 mg, 80% yield) as a red solid. LC-MS (m/z) 548 (M+1).

EXAMPLE 20

Preparation of 6-(5-((((4-methyl-2-oxoindolin-3-ylidene)hydrazono)methyl)-2,4-dimethyl-1H-pyrrole-3-carboxamido)-N-(2-aminophenyl)hexanamide

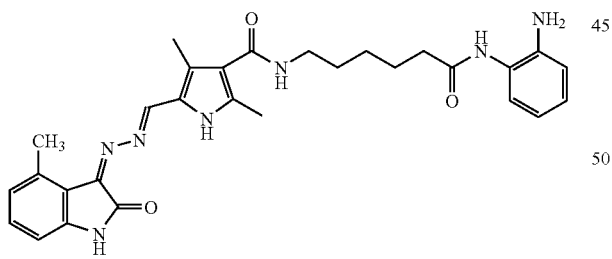

6-(5-(((4-methyl-2-oxoindolin-3-ylidene)hydrazono)methyl)-2,4-dimethyl-1H-pyrrole-3-carboxamido)-hexanoic acid (437 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (427 mg, 81% yield) as a red solid. LC-MS (m/z) 528 (M+1).

EXAMPLE 21

Preparation of 6-(5-((((5-nitro-2-oxoindolin-3-ylidene)hydrazono)methyl)-2,4-dimethyl-1H-pyrrole-3-carboxamido)-N-(2-aminophenyl)hexanamide

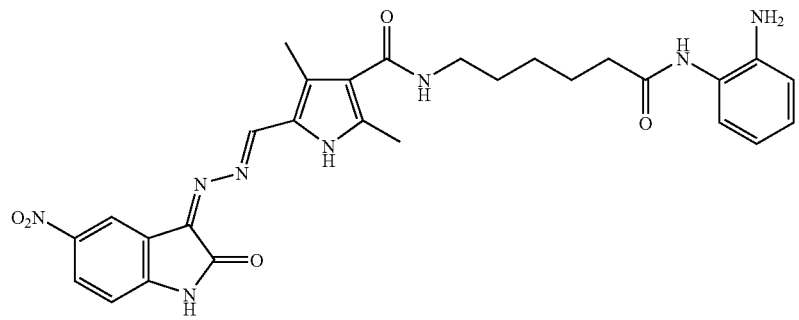

6-(5-(((5-nitro-2-oxoindolin-3-ylidene)hydrazono)methyl)-2,4-dimethyl-1H-pyrrole-3-carboxamido)-hexanoic acid (468 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (402 mg, 72% yield) as a red solid. LC-MS (m/z) 559 (M+1).

EXAMPLE 22

Preparation of 6-(5-(((6-methoxy-2-oxoindolin-3-ylidene)hydrazono)methyl)-2,4-dimethyl-1H-pyrrole-3-carboxamido)-N-(2-aminophenyl)hexanamide

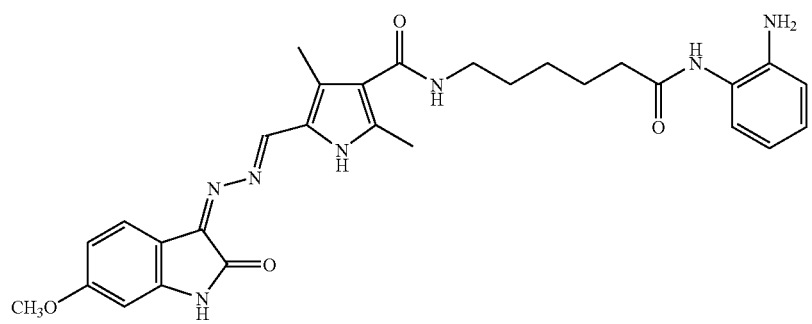

6-(5-(((6-methoxy-2-oxoindolin-3-ylidene)hydrazono)methyl)-2,4-dimethyl-1H-pyrrole-3-carboxamido)-hexanoic acid (453 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (408 mg, 75% yield) as a red solid. LC-MS (m/z) 544 (M+1).

EXAMPLE 23

Preparation of 6-(5-(((6-trifluoromethyl-2-oxoindolin-3-ylidene)hydrazono)methyl)-2,4-dimethyl-1H-pyrrole-3-carboxamido)-N-(2-aminophenyl)hexanamide

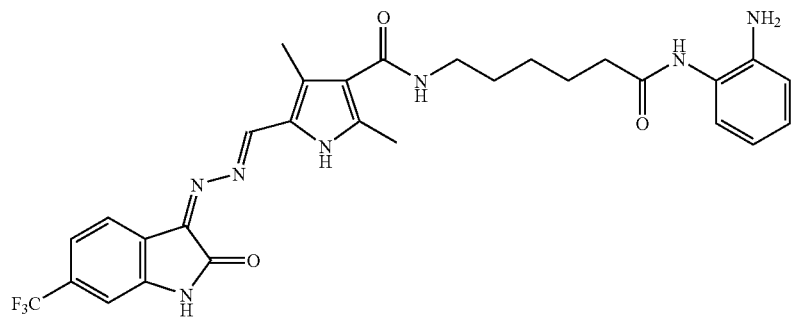

6-(5-(((6-trifluoromethyl-2-oxoindolin-3-ylidene)hydrazono)methyl)-2,4-dimethyl-1H-pyrrole-3-carboxamido)-hexanoic acid (491 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (384 mg, 66% yield) as a red solid. LC-MS (m/z) 582 (M+1).

EXAMPLE 24

Preparation of 8-(5-(((5-fluoro-2-oxoindolin-3-ylidene)hydrazono)methyl)-2,4-dimethyl-1H-pyrrole-3-carboxamido)-octanoic acid methyl ester

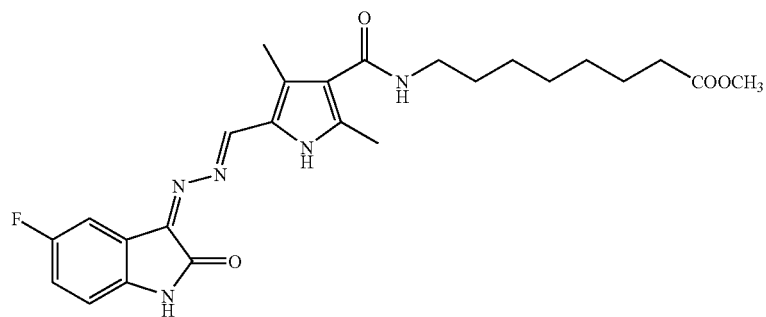

5-(((5-fluoro-2-oxoindolin-3-ylidene)hydrazono)methyl)-2,4-dimethyl-1H-pyrrole-3-carboxylic acid (328 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 8-aminocaprylic acid methyl ester hydrochloride (251 mg, 1.2 mmol) were added. The mixture was stirred for 24 hours at room temperature. The mixture was diluted with 400 mL of brine. The solids were collected by vacuum filtration, washed with water and dried under vacuum to give the title compound (287 mg, 63% yield) as a red solid. LC-MS (m/z) 484 (M+1).

EXAMPLE 25

Preparation of 8-(5-(((5-fluoro-2-oxoindolin-3-ylidene)hydrazono)methyl)-2,4-dimethyl-1H-pyrrole-3-carboxamido)-octanoic acid

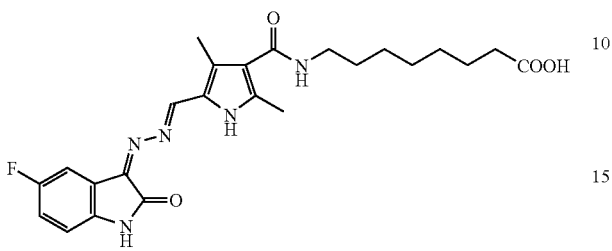

8-(5-(((5-fluoro-2-oxoindolin-3-ylidene)hydrazono)methyl)-2,4-dimethyl-1H-pyrrole-3-carboxamido)-octanoic acid methyl ester (483 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (159 mg, 34% yield) as a red solid. LC-MS (m/z) 470 (M+1).

EXAMPLE 26

Preparation of 8-(5-(((5-fluoro-2-oxoindolin-3-ylidene)hydrazono)methyl)-2,4-dimethyl-1H-pyrrole-3-carboxamido)-N-hydroxyoctanamide

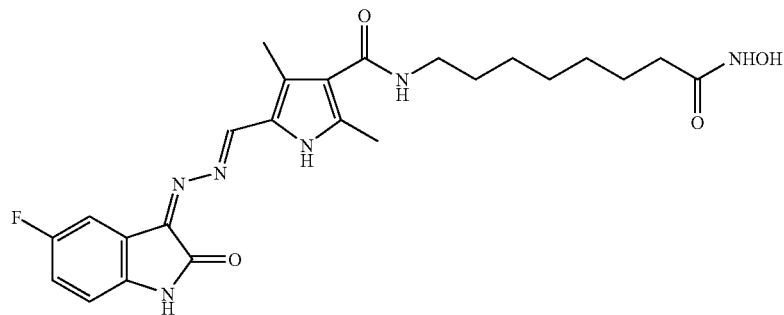

8-(5-(((5-fluoro-2-oxoindolin-3-ylidene)hydrazono)methyl)-2,4-dimethyl-1H-pyrrole-3-carboxamido)-octanoic acid (469 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (237 mg, 49%) as a red solid. LC-MS (m/z) 485 (M+1).

EXAMPLE 27

Preparation of 8-(5-((((5-fluoro-2-oxoindolin-3-ylidene)hydrazono)methyl)-2,4-dimethyl-1H-pyrrole-3-carboxamido)-N-(2-amino-4-fluorophenyl)octanamide

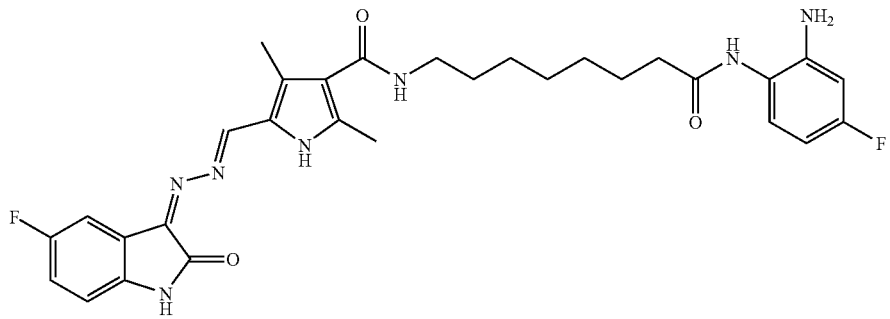

8-(5-(((5-fluoro-2-oxoindolin-3-ylidene)hydrazono)methyl)-2,4-dimethyl-1H-pyrrole-3-carboxamido)-octanoic acid (469 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (386 mg, 67% yield) as a red solid. LC-MS (m/z) 578 (M+1).

EXAMPLE 28

Preparation of 8-(5-((((5-fluoro-2-oxoindolin-3-ylidene)hydrazono)methyl)-2,4-dimethyl-1H-pyrrole-3-carboxamido)-N-(2-aminophenyl)octanamide

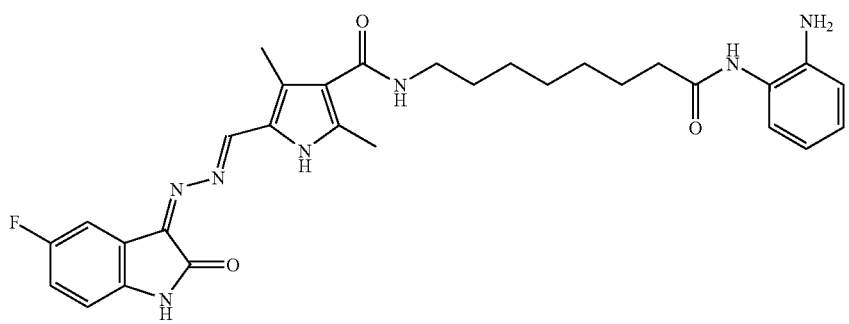

8-(5-(((5-fluoro-2-oxoindolin-3-ylidene)hydrazono)methyl)-2,4-dimethyl-1H-pyrrole-3-carboxamido)-octanoic acid (469 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (402 mg, 72% yield) as a red solid. LC-MS (m/z) 560 (M+1).

EXAMPLE 29

Preparation of 6-(4-(((5-fluoro-2-oxoindolin-3-ylidene)hydrazono)methyl)benzamido)-hexanoic acid methyl ester

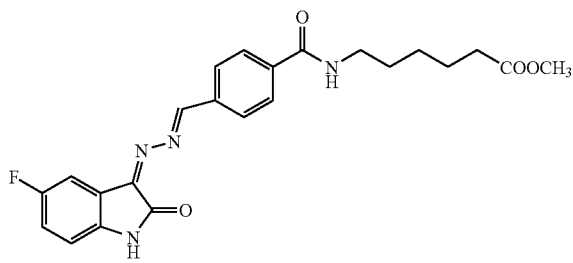

4-(((5-fluoro-2-oxoindolin-3-ylidene)hydrazono)methyl)benzoic acid (311 mg, 1 mmol) and 8 ml of DMF were stirred at room temperature while 1-Ethyl-3-(3-dimethylaminopropyl)-carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (114 mg, 28% yield) as a brown solid. LC-MS (m/z) 439 (M+1).

EXAMPLE 30

Preparation of 6-(4-(((5-fluoro-2-oxoindolin-3-ylidene)hydrazono)methyl)benzamido)-hexanoic acid 6-(4-(((5-fluoro-2-oxoindolin-3-ylidene)hydrazono)methyl)benzamido)hexanoic acid methyl ester (438 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (119 mg, 28% yield) as a brown solid. LC-MS (m/z) 425 (M+1).

EXAMPLE 31

Preparation of 6-(4-(((5-fluoro-2-oxoindolin-3-ylidene)hydrazono)methyl)benzamido)-N-hydroxy-hexanamide

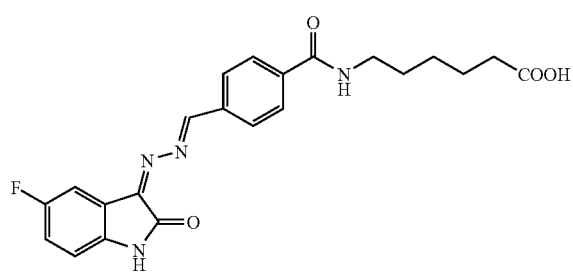

6-(4-(((5-fluoro-2-oxoindolin-3-ylidene)hydrazono)methyl)benzamido)hexanoic acid (424 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (224 mg, 51%) as a brown solid. LC-MS (m/z) 440 (M+1).

EXAMPLE 32

Preparation of 6-(4-(((5-fluoro-2-oxoindolin-3-ylidene)hydrazono)methyl)benzamido)-N-(2-aminophenyl)hexanamide

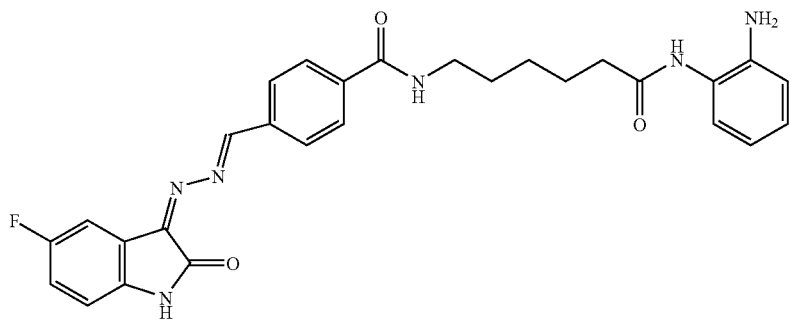

6-(4-(((5-fluoro-2-oxoindolin-3-ylidene)hydrazono)methyl)benzamido)hexanoic acid (424 mg, 1 mmol), and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (375 mg, 73% yield) as a brown solid. LC-MS (m/z) 515 (M+1).

EXAMPLE 33

Preparation of 8-(4-(((5-fluoro-2-oxoindolin-3-ylidene)hydrazono)methyl)benzamido)-octanoic acid methyl ester

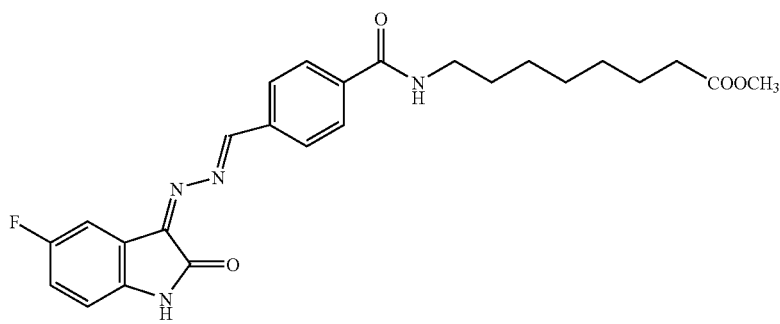

4-(((5-fluoro-2-oxoindolin-3-ylidene)hydrazono)methyl)benzoic acid (311 mg, 1 mmol) and 8 ml of DMF were stirred at room temperature while 1-Ethyl-3-(3-dimethylaminopropyl)-carbodiimide hydrochloride (394 mg, 2 mmol), hydroxybenzo-triazole (162 mg, 1.2 mmol), triethylamine (404 mg, 4 mmol) and 8-aminocaprylic acid methyl ester hydrochloride (251 mg, 1.2 mmol) were added. The mixture was stirred for 24 hours at room temperature. The mixture was diluted with 400 mL of brine. The solids were collected by vacuum filtration, washed with water and dried under vacuum to give the title compound (290 mg, 62% yield) as a brown solid. LC-MS (m/z) 467 (M+1).

EXAMPLE 34

Preparation of 8-(4-(((5-fluoro-2-oxoindolin-3-ylidene)hydrazono)methyl)benzamido)-octanoic acid

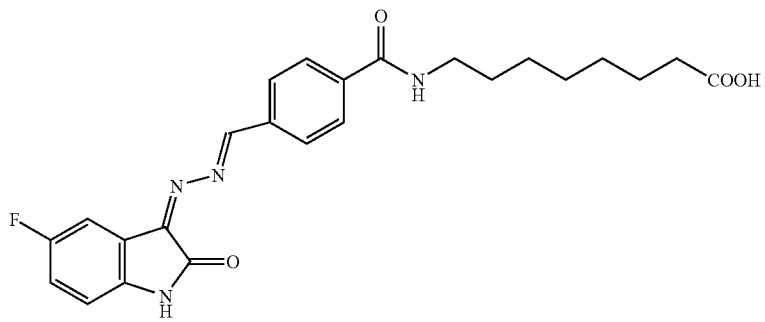

8-(4-(((5-fluoro-2-oxoindolin-3-ylidene)hydrazono)methyl)benzamido)octanoic acid methyl ester (466 mg, 1 mmol) and 300ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (149 mg, 33% yield) as a brown solid. LC-MS (m/z) 453 (M+1).

EXAMPLE 35

Preparation of 8-(4-(((5-fluoro-2-oxoindolin-3-ylidene)hydrazono)methyl)benzamido)-N-(2-aminophenyl)octanamide

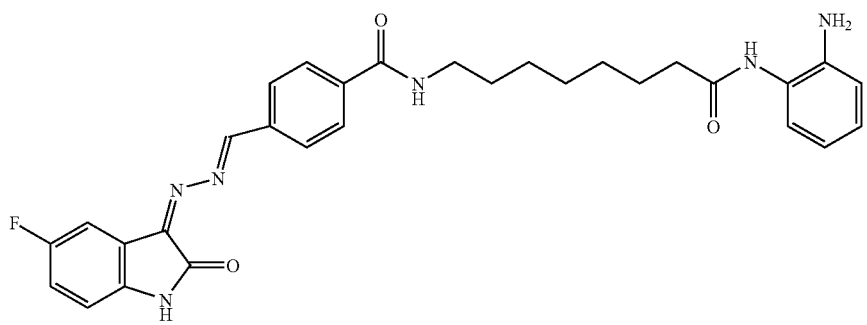

8-(4-(((5-fluoro-2-oxoindolin-3-ylidene)hydrazono)methyl)benzamido)octanoic acid (452 mg, 1 mmol), and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (423 mg, 72% yield) as a brown solid. LC-MS (m/z) 543 (M+1).

EXAMPLE 36

Preparation of 8-(4-(((5-fluoro-2-oxoindolin-3-ylidene)hydrazono)methyl)benzamido)-N-(2-amino-4-fluorophenyl)octanamide

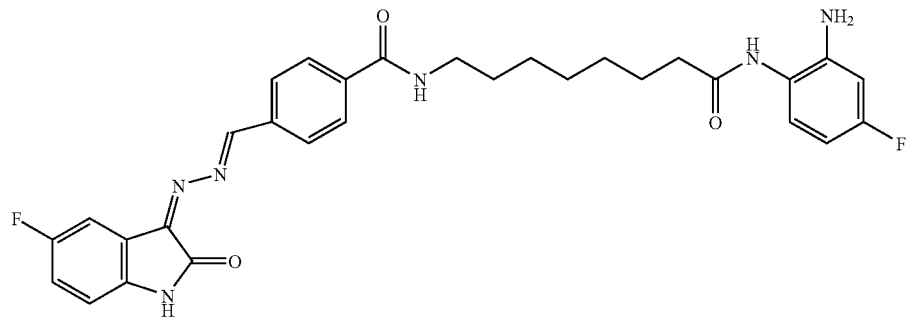

8-(4-(((5-fluoro-2-oxoindolin-3-ylidene)hydrazono)methyl)benzamido)octanoic acid (452 mg, 1 mmol), and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (358 mg, 64% yield) as a brown solid. LC-MS (m/z) 561 (M+1).

EXAMPLE 37

Preparation of 6-(4-((5-fluoro-2-oxoindolin-3-ylidene)methyl)benzamido)-hexanoic acid methyl ester

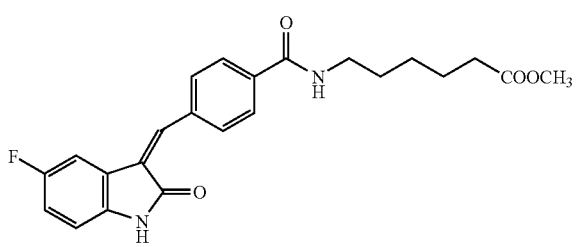

4-((5-fluoro-2-oxoindolin-3-ylidene)methyl)benzoic acid (283 mg, 1 mmol) and 8 ml of DMF were stirred at room temperature while 1-Ethyl-3-(3-dimethylaminopropyl)-carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (362 mg, 88% yield) as a brown solid. LC-MS (m/z) 411 (M+1).

EXAMPLE 38

Preparation of 6-(4-((5-fluoro-2-oxoindolin-3-ylidene)methyl)benzamido)-hexanoic acid

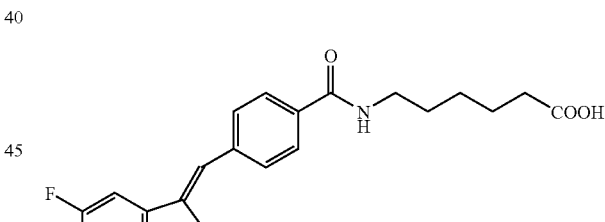

6-(4-((5-fluoro-2-oxoindolin-3-ylidene)methyl)benzamido)hexanoic acid methyl ester (410 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (305 mg, 77% yield) as a brown solid. LC-MS (m/z) 397 (M+1).

EXAMPLE 39

Preparation of 6-(4-((5-fluoro-2-oxoindolin-3-ylidene)methyl)benzamido)-N-(2-aminophenyl)hexanamide

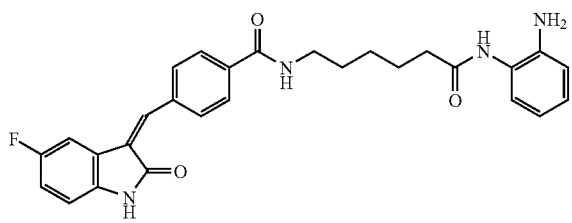

6-(4-((5-fluoro-2-oxoindolin-3-ylidene)methyl)benzamido)hexanoic acid (396 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (394 mg, 81% yield) as a brown solid.

$^1$H NMR (DMSO-d$_6$)δ1.38 (m, 2H, CH$_2$), 1.54 (m, 2H, CH$_2$), 1.60 (m, 2H, CH$_2$), 2.32 (t, J=8.0 Hz, 2H, CH$_2$CO), 3.28 (m, 2H, NCH$_2$), 4.80 (s, 2H, benzene-NH$_2$), 6.52 (t, J=8.0 Hz, 1H, Ar—H), 6.69 (d, J=8.0 Hz, 1H, Ar—H), 6.86 (m, 2H, Ar—H), 7.14 (m, 2H, Ar—H), 7.71 (s, 1H, vinyl-H), 7.76 (m, 1H, Ar—H), 7.92 (m, 1H, Ar—H), 7.96 (m, 1H, Ar—H), 8.39 (d, J=8.0 Hz, 1H, Ar—H), 8.50 (m, 1H, Ar—H), 9.09 (s, 1H, benzene-NH), 10.68 (s, 1H, CONH). LC-MS (m/z) 487 (M+1).

EXAMPLE 40

Preparation of 6-(4-((5-fluoro-2-oxoindolin-3-ylidene)methyl)benzamido)-N-(2-amino-4-fluorophenyl)hexanamide

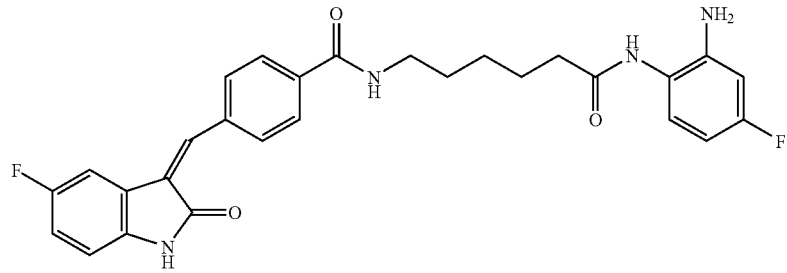

6-(4-((5-fluoro-2-oxoindolin-3-ylidene)methyl)benzamido)hexanoic acid (396 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (348 mg, 69% yield) as a brown solid. $^1$H NMR (DMSO-d$_6$)δ1.36 (m, 2H, CH$_2$), 1.60 (m, 2H, CH$_2$), 1.60 (m, 2H, CH$_2$), 2.30 (t, J=8.0 Hz, 2H, CH$_2$CO), 3.29 (m, 2H, NCH$_2$), 5.12 (s, 2H, benzene-NH$_2$), 6.27 (t, J=8.0 Hz, 1H, Ar—H), 6.46 (dd, J=4.0 Hz and 8.0 Hz, 1H, Ar—H), 6.88 (m, 1H, Ar—H), 7.10 (m, 2H, Ar—H), 7.71 (s, 1H, vinyl-H), 7.77 (m, 1H, Ar—H), 7.92 (m, 1H, Ar—H), 7.96 (m, 1H, Ar—H), 8.39 (d, J=8.0 Hz, 1H, Ar—H), 8.50 (m, 1H, Ar—H), 9.01 (s, 1H, benzene-NH), 10.68 (s, 1H, CONH). LC-MS (m/z) 505 (M+1).

EXAMPLE 41

Preparation of 6-(4-((5-fluoro-2-oxoindolin-3-ylidene)methyl)benzamido)-N-hydroxyhexanamide

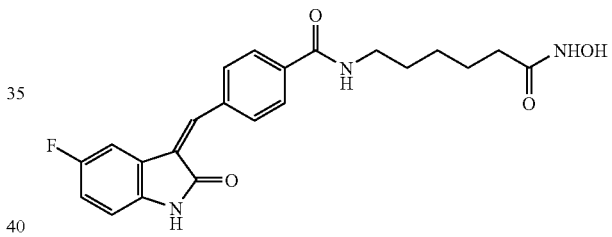

6-(4-((5-fluoro-2-oxoindolin-3-ylidene)methyl)benzamido)hexanoic acid (396 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (189 mg, 46%) as a brown solid. LC-MS (m/z) 412 (M+1).

EXAMPLE 42

Preparation of 6-(3-((5-fluoro-2-oxoindolin-3-ylidene)methyl)benzamido)-hexanoic acid methyl ester

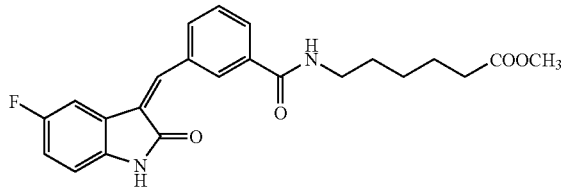

3-((5-fluoro-2-oxoindolin-3-ylidene)methyl)benzoic acid (283 mg, 1 mmol) and 8 ml of DMF were stirred at room temperature while 1-Ethyl-3-(3-dimethylaminopropyl)-carbodiimide hydrochloride (394 mg, 2 mmol), hydroxybenzotriazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (332 mg, 81% yield) as a brown solid. LC-MS (m/z) 411 (M+1).

EXAMPLE 43

Preparation of 6-(3-((5-fluoro-2-oxoindolin-3-ylidene)methyl)benzamido)-hexanoic acid

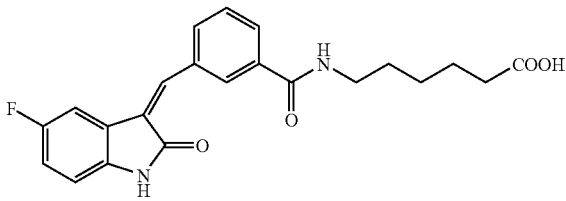

6-(3-((5-fluoro-2-oxoindolin-3-ylidene)methyl)benzamido)hexanoic acid methyl ester (410 mg, 1 mmol) and 300 ml of $CH_3OH$ were stirred at room temperature while 25 ml of 4 N solution of LiOH in $H_2O$ was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (289 mg, 73% yield) as a brown solid. LC-MS (m/z) 397 (M+1).

EXAMPLE 44

Preparation of 6-(3-((5-fluoro-2-oxoindolin-3-ylidene)methyl)benzamido)-N-(2-aminophenyl)hexanamide

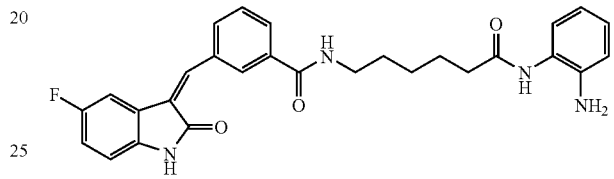

6-(3-((5-fluoro-2-oxoindolin-3-ylidene)methyl)benzamido)hexanoic acid (396 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (379 mg, 78% yield) as a brown solid. $^1$H NMR (DMSO-$d_6$) δ1.36 (m, 2H, $CH_2$), 1.59 (m, 4H, $CH_2$), 2.30 (t, J=8.0 Hz, 2H, $CH_2CO$), 3.29 (t, J=8.0 Hz, 2H, $NCH_2$), 4.80 (s, 2H, benzene-$NH_2$), 6.50 (t, J=8.0 Hz, 1H, Ar—H), 6.69 (d, J=8.0 Hz, 1H, Ar—H), 6.87 (m, 2H, Ar—H), 7.12 (m, 2H, Ar—H), 7.54 (d, J=8.0 Hz, 1H, Ar—H), 7.64 (m, 1H, Ar—H), 7.73 (s, 0.6 H, vinyl-H), 7.83 (m, 1H, Ar—H), 7.94 (m, 1H, Ar—H), 8.15 (s, 0.4 H, vinyl-H), 8.57 (m, 1H, Ar—H), 9.08 (s,1H, benzene-NH), 10.68 (s, 1H, CONH). LC-MS (m/z) 487 (M+1).

EXAMPLE 45

Preparation of 6-(3-((5-fluoro-2-oxoindolin-3-ylidene)methyl)benzamido)-N-(2-amino-4-fluorophenyl)hexanamide

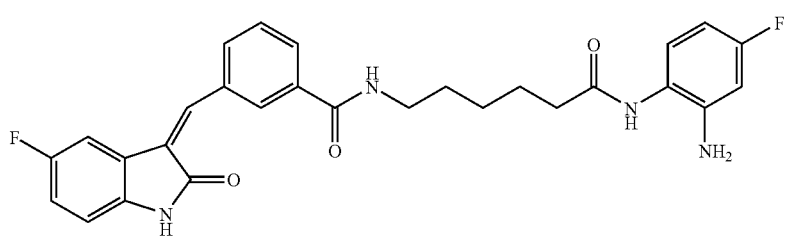

6-(3-((5-fluoro-2-oxoindolin-3-ylidene)methyl)benzamido)hexanoic acid (396 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (373 mg, 74% yield) as a brown solid. $^1$H NMR (DMSO-d$_6$)δ1.36 (m, 2H, CH$_2$), 1.59 (m, 4H, CH$_2$), 2.30 (t, J=8.0 Hz, 2H, CH$_2$CO), 3.28 (t, J=8.0 Hz, 2H, NCH$_2$), 5.12 (s, 2H, benzene-NH$_2$), 6.26 (t, J=8.0 Hz, 1H, Ar—H), 6.46 (d, J=8.0 Hz, 1H, Ar—H), 6.87 (m, 1H, Ar—H), 7.12 (m, 3H, Ar—H), 7.64 (m, 1H, Ar—H), 7.73 (s, 0.6×1H, vinyl-H), 7.83 (m, 1H, Ar—H), 7.94 (m, 1H, Ar—H), 8.16 (s, 0.4×1H, vinyl-H), 8.57 (m, 1H, Ar—H), 9.02 (s, 1H, benzene-NH), 10.68 (s, 1H, CONH). LC-MS (m/z) 505 (M+1).

EXAMPLE 46

Preparation of 6-(3-((5-fluoro-2-oxoindolin-3-ylidene)methyl)benzamido)-N-hydroxyhexanamide

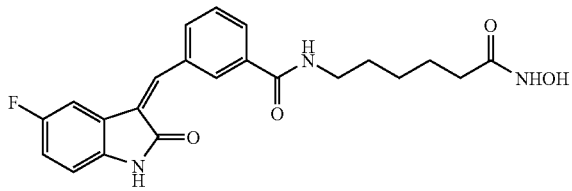

6-(3-((5-fluoro-2-oxoindolin-3-ylidene)methyl)benzamido)hexanoic acid (396 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (168 mg, 41%) as a brown solid. LC-MS (m/z) 412 (M+1).

EXAMPLE 47

Preparation of 5-(3-((5-fluoro-2-oxoindolin-3-ylidene)methyl)benzamido)-pentanoic acid methyl ester

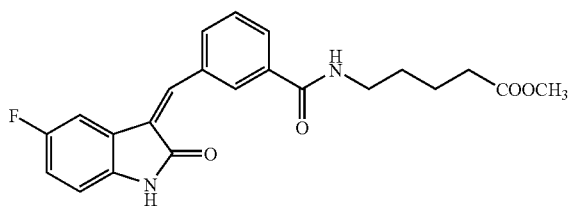

3-((5-fluoro-2-oxoindolin-3-ylidene)methyl)benzoic acid (283 mg, 1 mmol) and 8 ml of DMF were stirred at room temperature while 1-Ethyl-3-(3-dimethylaminopropyl)-carbodiimide hydrochloride (394 mg, 2 mmol), hydroxybenzotriazole (162 mg, 1.2 mmol), triethylamine (404 mg, 4 mmol) and 5-aminovaleric acid methyl ester hydrochloride (202 mg, 1.2 mmol) were added. The mixture was stirred for 24 hours at room temperature. The mixture was diluted with 400 mL of brine. The solids were collected by vacuum filtration, washed with water and dried under vacuum to give the title compound (337 mg, 89% yield) as a brown solid. LC-MS (m/z) 397 (M+1).

EXAMPLE 48

Preparation of 5-(3-((5-fluoro-2-oxoindolin-3-ylidene)methyl)benzamido)-pentanoic acid

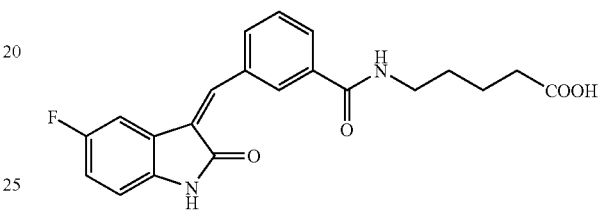

5-(3-((5-fluoro-2-oxoindolin-3-ylidene)methyl)benzamido)pentanoic acid methyl ester (396 mg, 1 mmol) and 300 ml of CH$_3$OH were stirred at room temperature while 25 ml of 4 N solution of LiOH in H$_2$O was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (294 mg, 77% yield) as a brown solid. LC-MS (m/z) 383 (M+1).

EXAMPLE 49

Preparation of 5-(3-((5-fluoro-2-oxoindolin-3-ylidene)methyl)benzamido)-N-(2-aminophenyl)pentanamide

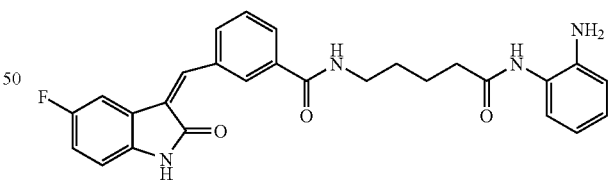

5-(3-((5-fluoro-2-oxoindolin-3-ylidene)methyl)benzamido)pentanoic acid (382 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (382 mg, 81% yield) as a brown solid. LC-MS (m/z) 473 (M+1).

EXAMPLE 50

Preparation of 5-(3-((5-fluoro-2-oxoindolin-3-ylidene)methyl)benzamido)-N-(2-amino-4-fluorophenyl)pentanamide

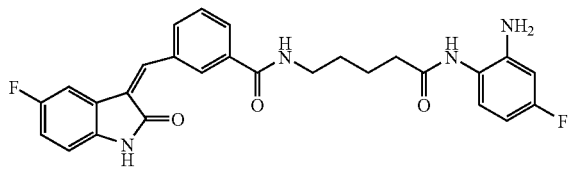

5-(3-((5-fluoro-2-oxoindolin-3-ylidene)methyl)benzamido)pentanoic acid (382 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (372 mg, 76% yield) as a brown solid. LC-MS (m/z) 491 (M+1).

EXAMPLE 51

Preparation of 5-(3-((5-fluoro-2-oxoindolin-3-ylidene)methyl)benzamido)-N-hydroxypentanamide

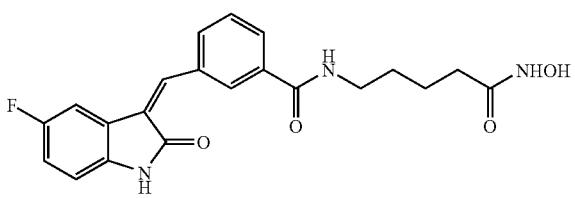

5-(3-((5-fluoro-2-oxoindolin-3-ylidene)methyl)benzamido)pentanoic acid (382 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (186 mg, 47%) as a brown solid. LC-MS (m/z) 398 (M+1).

EXAMPLE 52

Preparation of 8-(3-((5-fluoro-2-oxoindolin-3-ylidene)methyl)benzamido)-octanoic acid methyl ester

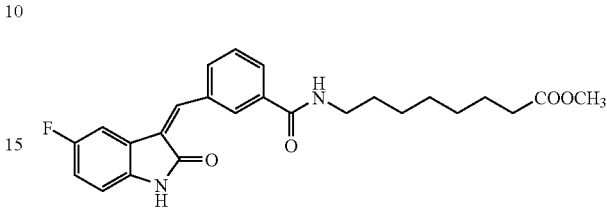

3-((5-fluoro-2-oxoindolin-3-ylidene)methyl)benzoic acid (283 mg, 1 mmol) and 8 ml of DMF were stirred at room temperature while 1-Ethyl-3-(3-dimethylaminopropyl)-carbodiimide hydrochloride (394 mg, 2 mmol), hydroxybenzotriazole (162 mg, 1.2 mmol), triethylamine (404 mg, 4 mmol) and 8-aminocaprylic acid methyl ester hydrochloride (251 mg, 1.2 mmol) were added. The mixture was stirred for 24 hours at room temperature. The mixture was diluted with 400 mL of brine. The solids were collected by vacuum filtration, washed with water and dried under vacuum to give the title compound (333 mg, 76% yield) as a brown solid. LC-MS (m/z) 439 (M+1).

EXAMPLE 53

Preparation of 8-(3-((5-fluoro-2-oxoindolin-3-ylidene)methyl)benzamido)-octanoic acid

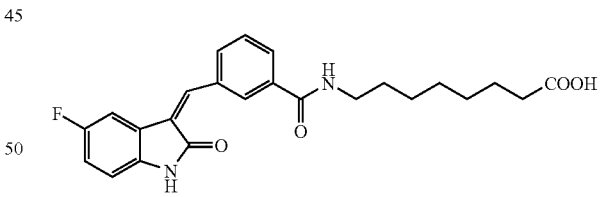

8-(3-((5-fluoro-2-oxoindolin-3-ylidene)methyl)benzamido)octanoic acid methyl ester (438 mg, 1 mmol) and 300 ml of CH$_3$OH were stirred at room temperature while 25 ml of 4 N solution of LiOH in H$_2$O was added. The mixture was stirred for 24 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (305 mg, 72% yield) as a brown solid. LC-MS (m/z) 425 (M+1).

EXAMPLE 54

Preparation of 8-(3-((5-fluoro-2-oxoindolin-3-ylidene)methyl)benzamido)-N-(2-aminophenyl)octanamide

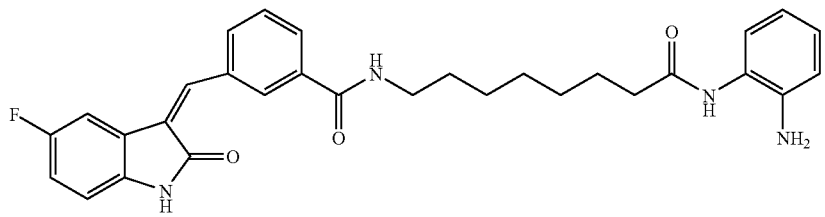

8-(3-((5-fluoro-2-oxoindolin-3-ylidene)methyl)benzamido)octanoic acid (424 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (426 mg, 83% yield) as a brown solid. LC-MS (m/z) 515 (M+1).

EXAMPLE 55

Preparation of 8-(3-((5-fluoro-2-oxoindolin-3-ylidene)methyl)benzamido)-N-(2-amino-4-fluorophenyl)octanamide

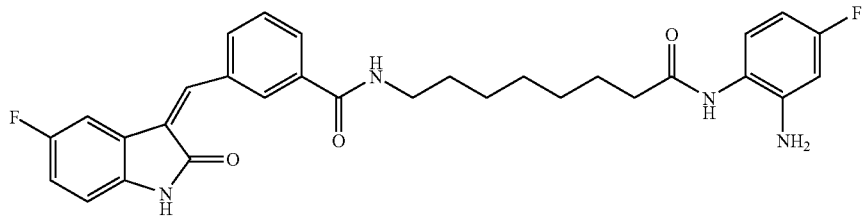

8-(3-((5-fluoro-2-oxoindolin-3-ylidene)methyl)benzamido)octanoic acid (424 mg, 1 mmol), and 8 ml of DMF were stirred at room temperature while 1-Ethyl-3-(3-dimethylamino-propyl)carbodiimide hydrochloride (394 mg, 2 mmol), hydroxybenzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (436 mg, 82% yield) as a brown solid. LC-MS (m/z) 533 (M+1).

EXAMPLE 56

Preparation of 8-(3-((5-fluoro-2-oxoindolin-3-ylidene)methyl)benzamido)-N-hydroxyoctanamide

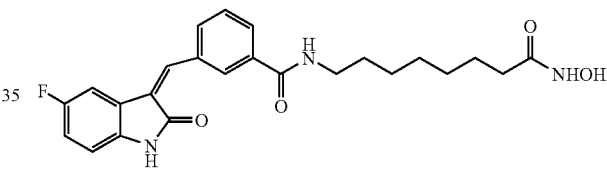

8-(3-((5-fluoro-2-oxoindolin-3-ylidene)methyl)benzamido)octanoic acid (424 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (224 mg, 51%) as a brown solid. LC-MS (m/z) 440 (M+1).

EXAMPLE 57

In vitro inhibition of total HDAC enzyme activity, inhibition of HDAC subtypes activity in cells by reporter gene assay, in cell acetylation of α-tubulin and lysine by compounds included in formula (I)

| Example (compound) | % of Inhibition on Total HDAC Enzyme at 30 μM | % of SAHA Response for HDAC class I at 10 μM (p21 reporter gene) | % of SAHA Response for HDAC3 at 10 μM (gdf11 reporter gene) | % of SAHA Response for HDAC4/5 at 10 μM (MEF2 reporter gene) | Fold Induction of α-tubulin acetylation (HDAC6) at 10 μM | % of SAHA Response for HDAC7 at 10 μM (Nur77 reporter gene) | Fold Induction of lysine acetylation at 10 μM |
|---|---|---|---|---|---|---|---|
| SAHA | 99% | 100% | 100% | 100% | 7.52 | 100% | 12.37 |
| 7 | 2% | 11% | 7% | 23% | 1.03 | 3% | 1.58 |
| 8 | −26% | 7% | 5% | 23% | 1.76 | 4% | 2.01 |
| 11 | 86% | 52% | 49% | 27% | 2.17 | 9% | 1.87 |
| 12 | 14% | 9% | 6% | 35% | 2.04 | 6% | 1.84 |
| 13 | 30% | 18% | 13% | 18% | 2.73 | 5% | 3.08 |
| 26 | 98% | 53% | 38% | 20% | 1.85 | 11% | 2.42 |
| 27 | 5% | 8% | 6% | 37% | 1.64 | 6% | 2.13 |
| 28 | 18% | 36% | 26% | 32% | 1.74 | 16% | 1.70 |
| 31 | 89% | 39% | 36% | 30% | 1.88 | 8% | 1.67 |
| 32 | 20% | 17% | 12% | 28% | 2.59 | 5% | 1.32 |
| 35 | 22% | 56% | 36% | 46% | 1.39 | 13% | 1.04 |
| 36 | −16% | 9% | 6% | 50% | 1.57 | 7% | 1.35 |
| 39 | 31% | 67% | 41% | 45% | 0.93 | 29% | 1.73 |
| 40 | 22% | 19% | 13% | 56% | 1.04 | 9% | 1.50 |
| 41 | 96% | 13% | 11% | 21% | 1.47 | 4% | 1.60 |
| 44 | 30% | 97% | 48% | 85% | 2.66 | 35% | 1.42 |
| 45 | 30% | 19% | 12% | 44% | 1.64 | 16% | 1.17 |
| 46 | 95% | 15% | 10% | 27% | 2.07 | 4% | 1.16 |
| 49 | 22% | 18% | 11% | 32% | 2.39 | 8% | 1.02 |
| 50 | −3% | 7% | 4% | 43% | 1.97 | 12% | 1.08 |
| 51 | 86% | 18% | 12% | 33% | 1.97 | 3% | 1.31 |
| 54 | 40% | 72% | 52% | 53% | 2.91 | 25% | 1.34 |
| 55 | 14% | 10% | 6% | 36% | 1.49 | 9% | 1.12 |
| 56 | 93% | 65% | 56% | 62% | 2.66 | 27% | 1.70 |

Measurement of in vitro inhibition of total HDAC enzyme activity:

The in vitro inhibition of total HDAC enzyme was determined by HDAC Fluorimetric Assay/Drug Discovery Kit (BIOMOL) according to manufacture's instruction.

1. Add Assay buffer, diluted trichostatin A or test inhibitor to appropriate wells of the microtiter plate. Following table lists examples of various assay types and the additions required for each test.

| Sample | Assay Buffer | HeLa Extract (Dilution) | Inhibitor (5x) | Fluor de Lys ™ Substrate (2x) |
|---|---|---|---|---|
| Blank (No Enzyme) | 25 μl | 0 | 0 | 25 μl |
| Control | 10 μl | 15 μl | 0 | 25 μl |
| Trichostatin A | 0 | 15 μl | 10 μl | 25 μl |
| Test Sample | 0 | 15 μl | 10 μl | 25 μl |

2. Add diluted HeLa extract or other HDAC sample to all wells except those that are to be "No Enzyme Controls" (Blank).
3. Allow diluted Fluor de LyS™ Substrate and the samples in the microtiter plate to equilibrate to assay temperature (25° C.).
4. Initiate HDAC reactions by adding diluted substrate (25 μl) to each well and mixing thoroughly.
5. Allow HDAC reactions to proceed for desired length of time and then stop them by addition of Fluor de Lys™ Developer (50 μl). Incubate plate at room temperature (25° C.) for 10-15 min.
6. Read samples in a microtiter-plate reading fluorimeter capable of excitation at a wavelength in the range 350-380 nm and detection of emitted light in the range 440-460 nm.

Measurement of inhibition of HDAC subtypes activity in cells by reporter gene assay: HDAC subtype selectivity inhibition assay of tested compounds was carried out by several reporter gene assays experiments. Briefly, HeLa cells were seeded in 96-well plates the day before transfection to give a confluence of 50-80%. Cells were transfected with one of reporter gene plasmids containing a promoter sequences or response elements upstream of a luciferase gene construct using FuGene6 transfection reagent according to the manufacturer's instructions (Roche). The promoters or response elements including p21-promoter, gdf11-promoter, MEF-binding element (MEF2), Nur77-promoter were fused upstream to the luciferase gene reporter construct. For normalizing the transfection efficiency, a GFP expression plasmid was cotransfected. Cells were allowed to express protein for 24 hours followed by addition of individual compounds or the vehicle (DMSO). 24 hours later, the cells were harvested and the luciferase assays were performed using the luciferase assay kit according to the manufacturer's instructions (Promega). To normalize the data from the luciferase assays, GFP activity from transfected cells was measured in a microtiter-plate reading fluorimeter capable of excitation at a wavelength at 485 nm and detection of emitted light at 527 nm.

Measurement of acetylation activity in cells on substrates:
ELISA assay of acetylation of α-tubulin
This assay is used to measure in vivo inhibition of HDAC6 in a cytoblot assay. Materials and Reagent:
1. 24-well tissue culture
2. DMEM Medium containing 10% FBS
3. 96-well white plate
4. HeLa cell line
5. M-PER Mammalian Protein Extraction Reagent (Pierce)
6. Bradford assay reagent
7. Anti-acetyl-tubulin (Upstate)
8. HRP-labeled anti-mouse IgG (Upstate)
9. Coating Buffer: 15 mM $Na_2CO_3$, 35 mM $NaHCO_3$ (pH 9.6)
10. 10×PBS: 0.58 M $Na_2HPO_4$, 0.17M $NaH_2PO_4$, 0.68M NaCl (pH 7.4)
11. Wash Buffer:1×PBS containing 0.05% Tween-20 (PBST)
12. Blocking Buffer:10 mg/ml bocine serum albumin (BSA) in PBS
13. Antibody Dilution Buffer: 5 mg/ml BSA in PBST
14. Enhanced chemiluminescence (ECL) (Amersham)
Procedure for performing the assay in 96-well plate:
1. HeLa cells were seeded at a density of 60000 cells/500 µl/well in 24-well plate and incubated at 37° C. for 24 hours.
2. Compounds were added and incubated for 24 hours at 37° C.
3. Culture medium was removed, then washes the cells twice with ice-cold PBS.
4. Add 100 µl/well of Protein Extraction Reagent and gently shake the mixture for 5 minutes.
5. Collect the lysate to a 96-well plate respectively. Determine the concentration of protein by Bradford assay.
6. Coat the wells of a 96-well white plate with 100 µl/well of 2.5 µg whole cell protein in Coating Buffer by incubating overnight at 4° C.
7. Discard the uncoated proteins and wash the coated wells three times with 200 µl/well of PBST.
8. Block coated wells by incubating the plate with 200 µl/well of Blocking Buffer for 1 hour at 37° C.
9. Wells were aspirated and washed three times with 200 µl/well of PBST.
10. After aspirating, 50 µl/well of Antibody Dilution Buffer containing anti-Ac-tubulin (1:1000) were added to each well and incubated for 2 hour at 37° C.
11. Wells were aspirated and washed three times with 200 µl/well of PBST.
12. 50 µl/well of Antibody Dilution Buffer containing HRP-labeled anti-mouse IgG (1:2000) were added to each well and incubated for 2 hour at 37° C.
13. Wells were aspirated and washed three times with 200 µl/well of PBST.
14. Wells were washed three times with 200 µl/well of purified water.
15. Add 50 µl/well of ECL mixture, then read the plates on the plate reader.

ELISA Assay of Acetylation of Lysine
This assay is used to measure in vivo inhibition of HDAC6 in a cytoblot assay.
Materials and Reagent:
1. 24-well tissue culture
2. DMEM Medium containing 10% FBS
3. 96-well white plate
4. HeLa cell line
5. M-PER Mammalian Protein Extraction Reagent (Pierce)
6. Bradford assay reagent
7. Acetylated-lysine polyclonal Antibody (Cell Signaling)
8. HRP-labeled anti-rabbit IgG (Upstate)
9. Coating Buffer: 15 mM $Na_2CO_3$, 35 mM $NaHCO_3$ (pH 9.6)
10. 10×PBS: 0.58M $Na_2HPO_4$, 0.17M $NaH_2PO_4$, 0.68M NaCl (pH 7.4)
11. Wash Buffer:1×PBS containing 0.05% Tween-20 (PBST)
12. Blocking Buffer:10 mg/ml bocine serum albumin (BSA) in PBS
13. Antibody Dilution Buffer: 5 mg/ml BSA in PBST
14. Enhanced chemiluminescence (ECL) (Amersham)
Procedure for performing the assay in 96-well plate:
1. HeLa cells were seeded at a density of 60000 cells/500 µl/well in 24-well plate and incubated at 37° C. for 24 hours.
2. Compounds were added and incubated for 24 hours at 37° C.
3. Culture medium was removed, then washes the cells twice with ice-cold PBS.
4. Add 100 µl/well of Protein Extraction Reagent and gently shake the mixture for 5 minutes.
5. Collect the lysate to a 96-well plate respectively. Determine the concentration of protein by Bradford assay.
6. Coat the wells of a 96-well white plate with 100 µl/well of 2.5 µg whole cell protein in Coating Buffer by incubating overnight at 4° C.
7. Discard the uncoated proteins and wash the coated wells three times with 200 µl/well of PBST.
8. Block coated wells by incubating the plate with 200 µl/well of Blocking Buffer for 1 hour at 37° C.
9. Wells were aspirated and washed three times with 200 µl/well of PBST.
10. After aspirating, 50 µl/well of Antibody Dilution Buffer containing acetylated-lysine polyclonal antibody (1:1000) were added to each well and incubated for 2 hour at 37° C.
11. Wells were aspirated and washed three times with 200 µl/well of PBST.
12. 50 µl/well of Antibody Dilution Buffer containing HRP-labeled anti-rabbit IgG (1:2000) were added to each well and incubated for 2 hour at 37° C.
13. Wells were aspirated and washed three times with 200 µl/well of PBST.
14. Wells were washed three times with 200 µl/well of purified water.
15. Add 50 µl/well of ECL mixture, then read the plates on the plate reader.

EXAMPLE 58

In vivo anti-cell proliferation by some compounds of formula (I)

| Example (compound) | $GI_{50}$ µM (Hut-78) | $GI_{50}$ µM (HL60) | $GI_{50}$ µM (HeLa) | $GI_{50}$ µM (A549) |
|---|---|---|---|---|
| 26 | 14.13 | 9.33 | 25.70 | 35.48 |
| 27 | 6.92 | 5.89 | >100 | >100 |
| 28 | 4.27 | 4.37 | 28.18 | 36.31 |
| 36 | 10.72 | 14.79 | 54.95 | 30.20 |
| 39 | 4.17 | 4.17 | 22.91 | 28.84 |
| 40 | 4.17 | 5.75 | 33.88 | 36.31 |
| 44 | 4.37 | 2.95 | 10.96 | 19.50 |
| 50 | 6.76 | 3.98 | 20.89 | 35.48 |
| 51 | nd | nd | nd | nd |
| 54 | 3.89 | 2.46 | 18.20 | 23.99 |
| 55 | nd | nd | nd | nd |
| 56 | 4.57 | 5.62 | 17.38 | 28.84 | nd: not determined;
Hut-78 is a human T lymphoma cell line;
HL60 is a human leukemia cell line;
HeLa is a human cervical cancer cell line;
A549 is a human lung cancer cell line Measurement of in vivo cell proliferation:
Tumor cells were trypsinized and plated into 96-well plates at 3,000 per well and incubated in complete medium with 10% FBS for 24 hours. Compounds were added over a final concentration range of 100 μmol/L to 100 nmol/L in 0.1% DMSO and incubated for 72 hours in complete medium. The effects on proliferation were determined by addition of MTS reagent (Promega) according to the instruction, incubation for 2 hours at 37° C. in $CO_2$ incubator, and record the absorbance at 490 nm using an ELISA plate reader.

What is claimed is:

1. An isolated compound of formula I:

(I)

wherein
X is =CH— or =N—N=CH—;
$R^1$, $R^2$, $R^3$ and $R^4$ are independently hydrogen, halo, alkyl, alkoxy, nitro or trifluoromethyl;
Ar is a benzene ring when X is =CH— or =N—N=CH—, or 2,4-dimethyl-1H-pyrrole when X is =N—N=CH—;
$R^5$ is —NHOH or $R^6$, $R^7$, $R^8$ and $R^9$ are independently hydrogen, halo, alkyl, alkoxy or trifluoromethyl; and
n is an integer ranging from 1 to 7.

2. A compound of claim 1, wherein X is =CH—;
$R^1$, $R^2$, $R^3$ and $R^4$ are independently hydrogen, halo, alkyl, alkoxy, nitro or trifluoromethyl;
Ar is a benzene ring;
$R^5$ is —NHOH; and
n is an integer ranging from 4 to 7.

3. A compound of claim 1, wherein X is =CH—;
$R^1$, $R^2$, $R^3$ and $R^4$ are independently hydrogen, halo, alkyl, alkoxy, nitro or trifluoromethyl;
Ar is a benzene ring;
$R^5$ is $R^6$, $R^7$, $R^8$ and $R^9$ are independently hydrogen, halo, alkyl, alkoxy or trifluoromethyl; and
n is an integer ranging from 4 to 7.

4. A compound of claim 1, wherein X is =N—N=CH—;
$R^1$, $R^2$, $R^3$ and $R^4$ are independently hydrogen, halo, alkyl, alkoxy, nitro or trifluoromethyl;
Ar is a benzene ring;
$R^5$ is —NHOH; and
n is an integer ranging from 4 to 7.

5. A compound of claim 1, wherein X is =N—N=CH—;
$R^1$, $R^2$, $R^3$ and $R^4$ are independently hydrogen, halo, alkyl, alkoxy, nitro or trifluoromethyl;
Ar is a benzene ring;
$R^5$ is $R^6$, $R^7$, $R^8$ and $R^9$ are independently hydrogen, halo, alkyl, alkoxy or trifluoromethyl; and
n is an integer ranging from 4 to 7.

6. A compound of claim 1, wherein X is =N—N=CH—;
$R^1$, $R^2$, $R^3$ and $R^4$ are independently hydrogen, halo, alkyl, alkoxy, nitro or trifluoromethyl;
Ar is 2,4-dimethyl-1H-pyrrole;
$R^5$ is —NHOH; and
n is an integer ranging from 4 to 7.

7. A compound of claim 1, wherein X is =N—N=CH—;
$R^1$, $R^2$, $R^3$ and $R^4$ are independently hydrogen, halo, alkyl, alkoxy, nitro or trifluoromethyl;
Ar is 2,4-dimethyl-1H-pyrrole;
$R^5$ is $R^6$, $R^7$, $R^8$ and $R^9$ are independently hydrogen, halo, alkyl, alkoxy or trifluoromethyl; and
n is an integer ranging from 4 to 7.

8. A process for the preparation of a compound of formula I (I)

wherein

X is =CH— or =N—N=CH—;

$R^1$, $R^2$, $R^3$ and $R^4$ are independently hydrogen, halo, alkyl, alkoxy, nitro or trifluoromethyl;

Ar is a benzene ring when X is =CH— or =N—N=CH—, or 2,4-dimethyl-1H-pyrrole when X is =N—N=CH—;

$R^5$ is —NHOH or

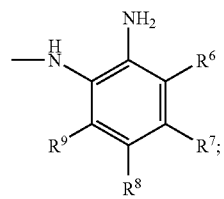

$R^6$, $R^7$, $R^8$ and $R^9$ are independently hydrogen, halo, alkyl, alkoxy or trifluoromethyl;

n is an integer ranging from 1 to 7;

a stereoisomer, enantiomer, diastereomer, or pharmaceutically acceptable salts thereof comprising the steps of:

(a) condensing compound 1 with compound 2 to give compound 3;

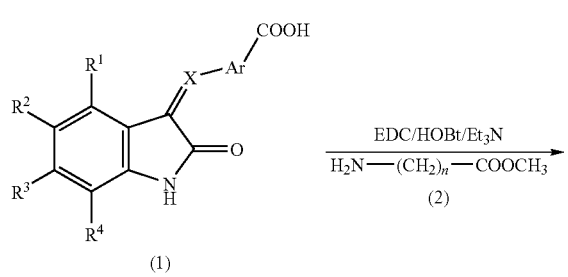

(b) hydrolyzing compound 3 with lithium hydroxide to give compound 4;

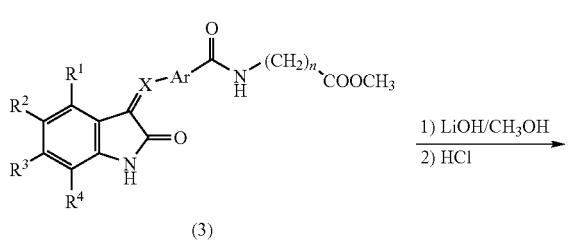

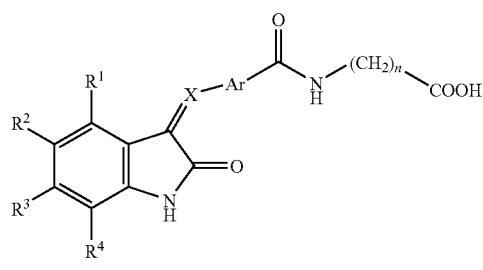

(c) condensing compound 4 with hydroxylamine to give compound 5a; and

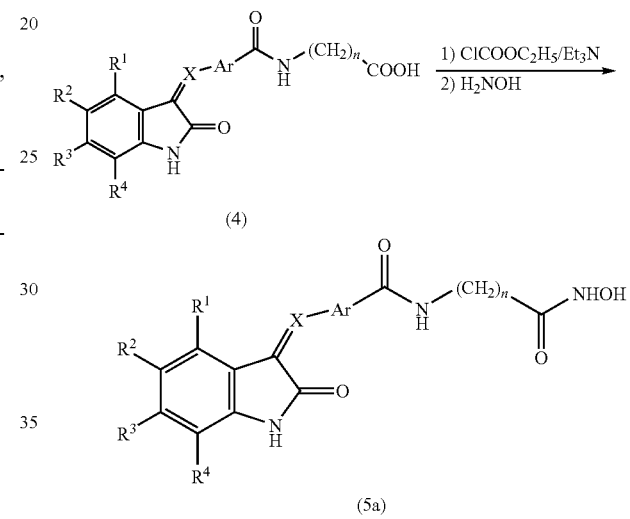

(d) condensing compound 4 with compound 6 to give compound 5b;

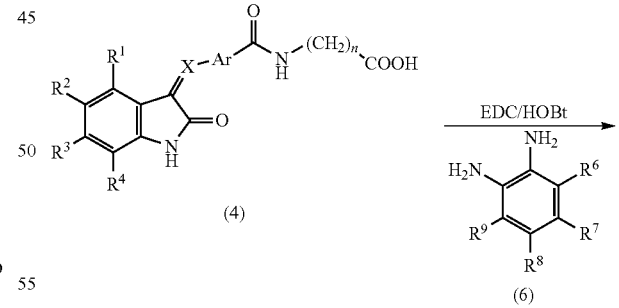

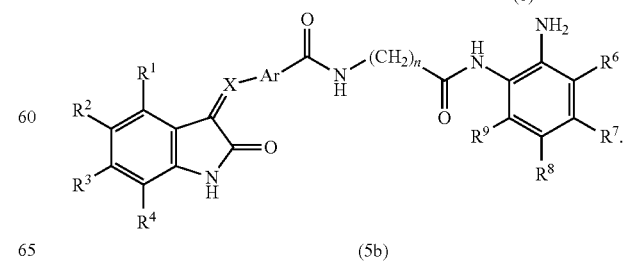

9. The process of claim 8, wherein the condensation reactions of steps (a) and (d) are conducted by using a peptide condensing agent, wherein said peptide condensing agent is 1-ethyl-3-(3-di-methyl-aminopropyl)carbodiimide, dicyclohexylcarbodiimide, or N,N'-carbonyldiimidazole.

10. The process of claim 8, wherein the condensation reaction of step (c) is conducted by using ClCOOEt as a condensing agent.

11. The process of claim 8, wherein the hydrolysis reaction of step (b) is conducted by using a hydrolysis agent.

12. The process of claim 11, wherein said hydrolysis agent is lithium hydroxide, sodium hydroxide, or potassium hydroxide.

13. A pharmaceutical composition comprising an effective amount of a compound according to claim 1 and at least one pharmaceutically acceptable excipient, carrier or diluent.

14. A dosage form unit of the pharmaceutical composition of claim 13 comprising an amount within the range of about 0.0001 to about 200 mg of said compound.

15. A pharmaceutical composition of claim 13 for administration by the oral, nasal, transdermal, pulmonary, or parenteral route.

16. A pharmaceutical composition, according to claim 13, suitable for administration to a human patient.

* * * * *

UNITED STATES PATENT AND TRADEMARK OFFICE
CERTIFICATE OF CORRECTION

PATENT NO. : 7,863,315 B2  Page 1 of 1
APPLICATION NO. : 12/353566
DATED : January 4, 2011
INVENTOR(S) : Xian-Ping Lu, Zhi-bin Li and Zhi-Qiang Ning It is certified that error appears in the above-identified patent and that said Letters Patent is hereby corrected as shown below:

Title Page; item (73);
Page 1, Assignee: Shenzhen Chipscreen Biosciences, Ltd., Shenzhen, Guangdong "(JP)" should read --(CN)--.

Signed and Sealed this
Fifth Day of April, 2011

David J. Kappos
*Director of the United States Patent and Trademark Office*